(12) United States Patent
Nayak et al.

(10) Patent No.: US 10,466,167 B2
(45) Date of Patent: Nov. 5, 2019

(54) METHODS AND SYSTEMS USING PHOTONIC CRYSTAL-BASED INTEGRATED COMPUTATIONAL ELEMENTS

(71) Applicant: Halliburton Energy Services, Inc., Houston, TX (US)

(72) Inventors: Aditya B. Nayak, Houston, TX (US); James M. Price, The Woodlands, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 393 days.

(21) Appl. No.: 15/505,070

(22) PCT Filed: Jun. 4, 2015

(86) PCT No.: PCT/US2015/034265
§ 371 (c)(1),
(2) Date: Feb. 17, 2017

(87) PCT Pub. No.: WO2016/195693
PCT Pub. Date: Dec. 8, 2016

(65) Prior Publication Data
US 2017/0276601 A1    Sep. 28, 2017

(51) Int. Cl.
*G01N 21/31* (2006.01)
*G01J 3/28* (2006.01)
(Continued)

(52) U.S. Cl.
CPC ............... *G01N 21/31* (2013.01); *F21V 9/04* (2013.01); *G01J 3/0205* (2013.01); *G01J 3/28* (2013.01);
(Continued)

(58) Field of Classification Search
CPC ..... G01N 21/13; G01N 21/31; G01N 21/3129; G01N 21/3133; G01N 21/3137;
(Continued)

(56) References Cited

U.S. PATENT DOCUMENTS 7,138,156 B1 * 11/2006 Myrick ................. G02B 5/285
427/10
7,521,769 B2 * 4/2009 Cunningham ......... G01N 21/00
257/414
(Continued)

FOREIGN PATENT DOCUMENTS

CN     102375914 A    3/2012
JP     2000267585 A   9/2000

OTHER PUBLICATIONS

Khalkhali et al., "Design of High-Q polystyrene nonlinear cavity for ultrafast all-optical switching in mid-infrared photonic crystal slabs with cavity-waveguide structure," Optics Communications, Sep. 2014, vol. 326, pp. 43-47.
(Continued)

*Primary Examiner* — Eric L Bolda
(74) *Attorney, Agent, or Firm* — Gilliam IP PLLC

(57) ABSTRACT

A method of fabricating an optical computing device using a photonic crystal-based integrated computational element is provided. The method includes selecting a photonic crystal structure with a design suite stored in a non-transitory, computer-readable medium and obtaining a transmission spectrum for the selected photonic crystal. Further, the method includes determining a predictive power of a photonic crystal-based integrated computational element for a characteristic of a sample using the transmission spectrum and a spectral database. And adjusting the transmission spectrum to improve a predictive power of the photonic crystal-based integrated computational element for measuring a characteristic of a sample being analyzed. Also,
(Continued)

fabricating the photonic crystal structure for the photonic crystal-based integrated computational element when the predictive power surpasses a pre-selected threshold.

23 Claims, 12 Drawing Sheets

(51) Int. Cl.
*G01J 3/02* (2006.01)
*G01J 3/36* (2006.01)
*G01J 3/46* (2006.01)
*G02B 5/28* (2006.01)
*B82Y 20/00* (2011.01)
*F21V 9/04* (2018.01)
*G02B 6/10* (2006.01)
*G02C 7/10* (2006.01)
*H01K 1/50* (2006.01)

(52) U.S. Cl.
CPC . *G01J 3/36* (2013.01); *G01J 3/46* (2013.01); *G02B 5/28* (2013.01); *G02B 6/10* (2013.01); *G02C 7/10* (2013.01); *H01K 1/50* (2013.01); *B82Y 20/00* (2013.01)

(58) Field of Classification Search
CPC .......... G01J 3/0205; G01J 3/28; G01J 3/2803; G01J 3/2866; G01J 3/36; G01J 3/46; B82Y 20/00; F21V 9/04; G02B 5/28
See application file for complete search history.

(56) References Cited

U.S. PATENT DOCUMENTS

| | | | |
|---|---|---|---|
| 8,798,414 | B2 | 8/2014 | Quan et al. |
| 9,097,649 | B2 * | 8/2015 | Simcock ............... G02B 5/285 |
| 2001/0012149 | A1 | 8/2001 | Lin et al. |
| 2002/0041749 | A1 * | 4/2002 | Johnson ................ B82Y 20/00 385/129 |
| 2003/0132705 | A1 | 7/2003 | Gee et al. |
| 2004/0207855 | A1 * | 10/2004 | Brady ..................... G01J 3/02 356/451 |
| 2006/0029349 | A1 * | 2/2006 | Hoshi ................... B82Y 20/00 385/129 |
| 2006/0243961 | A1 | 11/2006 | Levi et al. |
| 2009/0323014 | A1 | 12/2009 | Cunningham et al. |
| 2010/0014077 | A1 * | 1/2010 | Khetani ................... G01J 3/02 356/301 |
| 2011/0019189 | A1 | 1/2011 | Crouse et al. |
| 2011/0128537 | A1 * | 6/2011 | Bond .................... B82Y 20/00 356/301 |
| 2012/0078523 | A1 * | 3/2012 | Letant .................. G01N 21/658 702/19 |
| 2012/0206726 | A1 * | 8/2012 | Pervez .................... G01J 3/02 356/402 |
| 2012/0258549 | A1 * | 10/2012 | Lu ..................... G01N 21/6428 436/501 |
| 2014/0178005 | A1 | 6/2014 | Zhang et al. |
| 2014/0270671 | A1 | 9/2014 | Mustafeez et al. |

OTHER PUBLICATIONS

Meade et al., "Existence of a photonic band gap in two dimensions," Applied Physics Letters, 1992, pp. 495-497.
Xiao et al., "Optical limitation in two-dimensional nonlinear photonic crystal with triangular lattice," Physics Letters A, Dec. 2006, vol. 359, No. 6, pp. 723-727.
International Search Report and Written Opinion from PCT/US2015/034265, dated Feb. 16, 2016, 12 pages.
ID Application Serial No. P00201707520, First Examination Report, dated Mar. 21, 2019, 3 pages.

* cited by examiner

METHODS AND SYSTEMS USING PHOTONIC CRYSTAL-BASED INTEGRATED COMPUTATIONAL ELEMENTS

BACKGROUND

Optical computing devices, also commonly referred to as "opticoanalytical devices." can be used to analyze and monitor the properties of a substance in real time. Such optical computing devices will often employ a processing element that optically interacts with the substance to determine quantitative and/or qualitative values of one or more physical or chemical properties of the substance. The processing element may include multilayered interference elements designed to operate over a continuum of wavelengths in the electromagnetic spectrum from the UV to mid-infrared (MIR) ranges, or any sub-set of that region. One type of processing element is an integrated computational element (ICE), also known as a multivariate optical element (MOE). Electromagnetic radiation that optically interacts with the ICE is modified to be readable by a detector such that an output of the detector can be correlated to the physical or chemical characteristic of the substance being analyzed.

Multilayered optical interference based elements can exhibit inefficiencies in optical transmission at wavelengths of interest. Also, multilayered optical interference based elements may exhibit transmission at wavelengths where complete blockage (zero transmission) is desirable. Further, the spectral resolution of multilayered optical interference based elements may be less optimal due to irregularities at the boundaries between adjacent layers and layer thickness fabrication errors. These deleterious factors combine to reduce the accuracy and predictive power of the ICE resulting from the multi-layer optical interference based element.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

In the figures, elements having the same or similar reference numerals refer to the same or similar function, or step, unless otherwise noted.

DETAILED DESCRIPTION

Figure 1A:
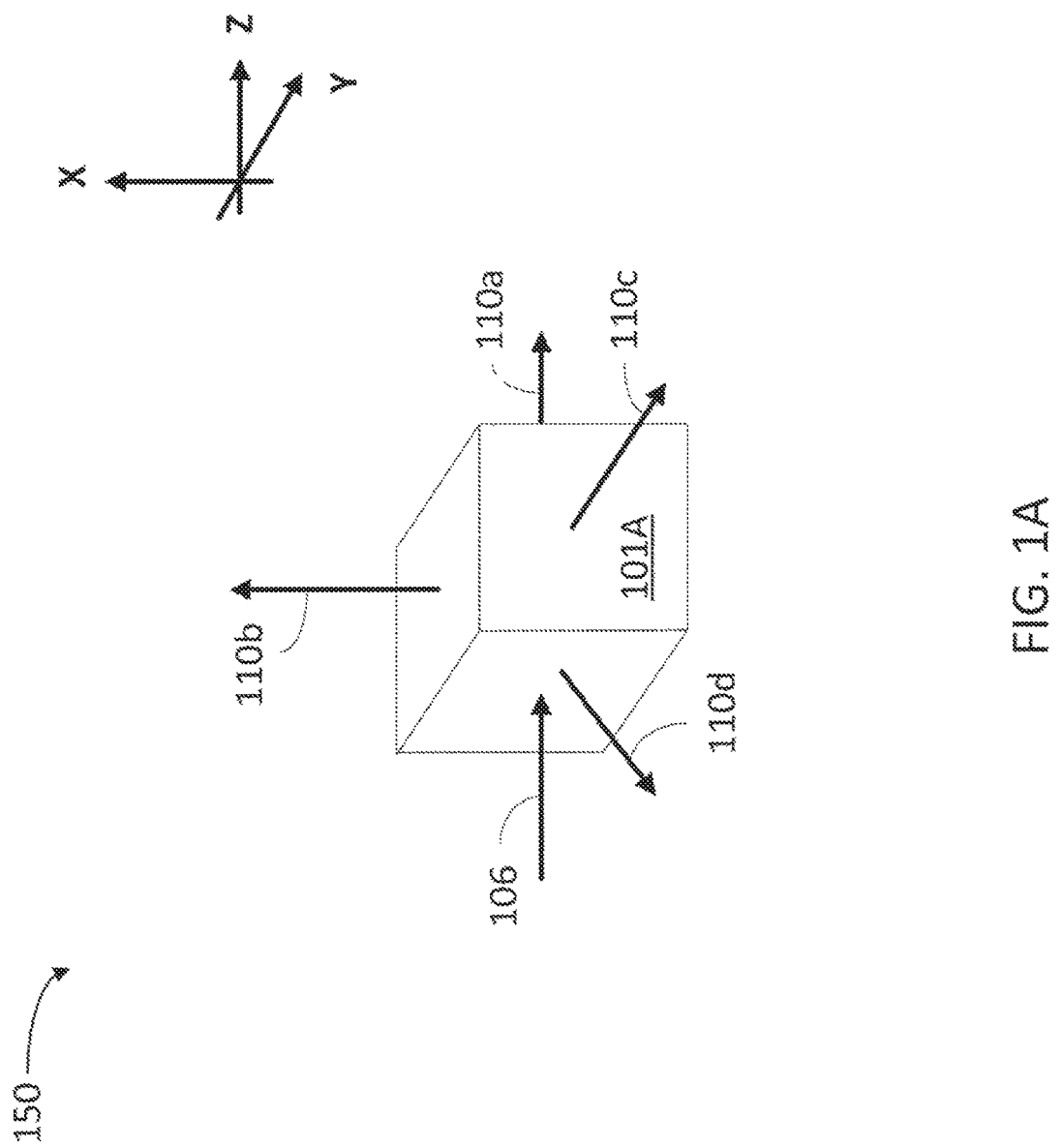
FIG. 1A illustrates a photonic crystal structure including a 3D substrate for use as an integrated computational element (ICE).

The present disclosure relates to fabrication and use of optical computing devices and, more particularly, to the fabrication and use of photonic crystal structures for generating more accurate optical elements for use in optical computing devices. The present disclosure facilitates the design, fabrication and delivery of accurate optical computing devices including photonic crystal (PhC)-based integrated computational elements (ICE). In some embodiments consistent with the present disclosure, an ICE may also be referred to as a multivariate optical computing element (MOE). PhC-based ICEs, as disclosed herein, operate with a higher predictive power as compared to devices including only multilayered interference elements.

The predictive power of a PhC-based ICE may be determined by measuring or estimating a Standard Error of Calibration (SEC), where values obtained with the PhC-based ICE are compared to true values in a calibrated sample set. Accordingly, the lower the SEC, the higher the predictive power of the PhC-based ICE. In some embodiments, the predictive power of a PhC-based ICE is determined by measuring sensitivity of the PhC-based ICE. The sensitivity may be proportional to a slope in a measurement curve. In some embodiments, the measurement curve relates an amplitude of the characteristic desired to be measured to a signal obtained from the PhC-based ICE. A higher sensitivity is generally associated with a higher predictive power of the PhC-based ICE. In some embodiments, the predictive power of a PhC-based ICE may be proportional to the Signal-to-Noise Ratio (SNR) of the signal obtained from the PhC-based ICE. Accordingly, a higher SNR may be associated with higher predictive power of the PhC-based ICE. More generally, embodiments consistent with the present disclosure may incorporate a merit function combining a SEC, sensitivity, and SNR as an indication of the predictive power of a PhC-based ICE.

Embodiments in this disclosure differ from previously disclosed attempts to design ICE by using a 2D or higher (e.g., 3D) photonic crystal. A 2D or higher photonic crystal has a complete photonic band-gap where certain wavelengths of light do not transmit, and also has resonant modes, i.e., narrowband transmission peaks. This type of design can achieve very high sensitivities because it can completely block unnecessary signals and only transmit relevant analyte related information which may be contained in several narrow bands of wavelengths across the wavelength range of interest.

As used herein, the term "characteristic" refers to a chemical, mechanical, or physical property of a substance. A characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be monitored with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device or sensor that is configured to receive an input of electromagnetic radiation associated with a substance and produce an output of electromagnetic radiation from a processing element arranged within the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components) or a substance being analyzed by the processing elements. Accordingly, optically interacted light refers to electromagnetic radiation that has been reflected, transmitted, scattered, diffracted, or absorbed by, emitted, or re-radiated, for example, using a processing element, but may also apply to interaction with a substance.

Embodiments disclosed herein include methods of fabricating a two-dimensional (2D) or a three-dimensional (3D) photonic crystal structure that provides a desirable spectral pattern response for measuring a physical or chemical property (i.e., a characteristic) of a substance being analyzed. In some embodiments, steps in a design stage provide an appropriate ICE selected according to an estimation of its predictive power. Some embodiments include obtaining a desired spectral pattern response for the ICE, and determining a selected photonic crystal structure that provides the desired spectral pattern response.

Systems and methods disclosed herein may be suitable for designing and fabricating ICE components for use in the oil and gas industry. It will be appreciated, however, that the various disclosed systems and methods are equally applicable to designing and fabricating ICE components for use in other technology fields including, but not limited to, the food and drug industry, industrial applications, mining industries, or any field where it may be advantageous to determine in real-time or near real-time a characteristic of a specific substance.

It has been found that the predictive power of an ICE in terms of its accuracy to determine a physical or chemical property of interest depends on the ability of the ICE to block a select portion of the spectrum, and transmit efficiently a different portion of the spectrum. The transmission range encompassing the highest transmission rate ('tm') and the lowest transmission rate ('to') constitutes the transmission 'dynamic range' of the ICE. Other relevant parameters for the predictive power of the ICE include its spectral resolution. The spectral resolution may be determined by the spectral width of a narrow band-pass portion of the ICE transmission spectrum. While the entire ICE transmission spectrum may include a broad range from a wavelength 'lo' to a wavelength 'lm,' at least in a portion of the spectrum a photonic crystal-based ICE as disclosed herein may desirably have a very narrow band-pass. In some embodiments lo may be in the lower end of the near-infrared (NIR) region (750, to 800 nm) and lm may be in the higher end of the NIR region (2000 to 2500 nm), and a narrow band-pass produced by a photonic crystal-based ICE may be as low as 1 nm or even less (0.5 nm, or less).

In some embodiments, PhC-based ICEs exhibiting an SEC of 10% or less, for example, may be considered "predictive," in a scale in which a SEC of 100% is perfectly "un-predictive" and a SEC of 0% is perfectly predictive. Likewise, photonic crystal-based ICEs exhibiting an SEC of greater than 2.00 may be considered "non-predictive." In other embodiments, resulting SEC values that determines whether a PhC-based ICE is predictive or not may be greater or less than 2.00, without departing from the scope of the disclosure. Those PhC-based ICEs considered non-predictive may be removed from consideration either by the operator or by software instructions carried out by a design suite, which may comprise software stored on a computer-readable medium containing program instructions configured to be executed by one or more processors of a computer system.

A fabrication computer program software may also be stored on a computer-readable medium containing program instructions configured to be executed by one or more processors of a computer system. The fabrication computer program may be configured to receive or otherwise download the specifications for a selected photonic crystal-based ICE as generated by the design suite and physically create a corresponding PhC-based ICE. In some embodiments, the fabrication computer program may also contain some of the same code used by the design suite such that it may be able to measure and report transmission spectrum signals of the fabrication steps not yet performed to compensate for any fabrication errors.

In some embodiments, a method includes selecting a PhC structure with a design suite stored in a non-transitory, computer-readable medium, obtaining a transmission spectrum for the selected PhC, and determining a predictive power of a PhC-based ICE for a characteristic of a sample with the transmission spectrum and a database of spectra for calibrated samples. The method may further include adjusting the transmission spectrum to improve the predictive power of a PhC-based ICE, and fabricating the PhC structure to be incorporated into the PhC-based ICE when the predictive power is above a pre-selected threshold.

In further embodiments, a method includes selecting a desired transmission spectrum for an ICE, identifying a PhC structure having a transmission spectrum comparable to the desired transmission spectrum, and determining a predictive power of a PhC-based ICE for a characteristic of a sample with the transmission spectrum and a database of spectra for calibrated samples. The method may further include adjusting the transmission spectrum of the PhC structure to improve a predictive power of a PhC-based ICE, and fabricating the PhC structure for the PhC-based ICE when the predictive power is above a pre-selected threshold.

In yet other embodiments, an ICE includes a PhC structure having an optical input side configured to receive an interacted light and an optical output side configured to receive an optical output. The PhC includes a medium having a first index of refraction, and a substrate embedded in the medium, the substrate having a second index of refraction and at least one geometric feature. In some embodiments, the at least one geometric feature is selected based on an output spectrum resulting from the optical output side. Further, according to some embodiments the optical output has an amplitude proportional to a scalar product of the interacted light and a regression vector for a characteristic of a sample being analyzed.

The features and advantages of the present disclosure will be readily apparent to those skilled in the art upon a reading of the description of the preferred embodiments that follows.

FIGS. 1A-1D illustrate different configurations of a PhC structure, according to embodiments consistent with the present disclosure. The PhC structure according to some embodiments may include a PhC of a dimensionality higher than one, such as a two-dimensional (2D) structure or a three-dimensional (3D) structure. A PhC operates as the optical analogue to a semi-conductor material for electric conduction. Atoms and molecules in a semi-conductor material are replaced by geometric features formed with materials having selected dielectric constants (complex refractive index of the material). In PhC structures, the periodic potential of a semiconductor crystal is replaced with a periodic dielectric function over a selected geometry. The refraction of light from the various interfaces in the selected geometry within the PhC produces a photonic band-gap for light propagating modes much in the same way as a conduction band-gap for charge carriers is formed in a semiconductor. A photonic band-gap prevents certain frequencies of light to propagate in certain directions. Examples of a 3D photonic crystal are shown in FIGS. 1A-1D, described in detail as follows.

Figure 1B:
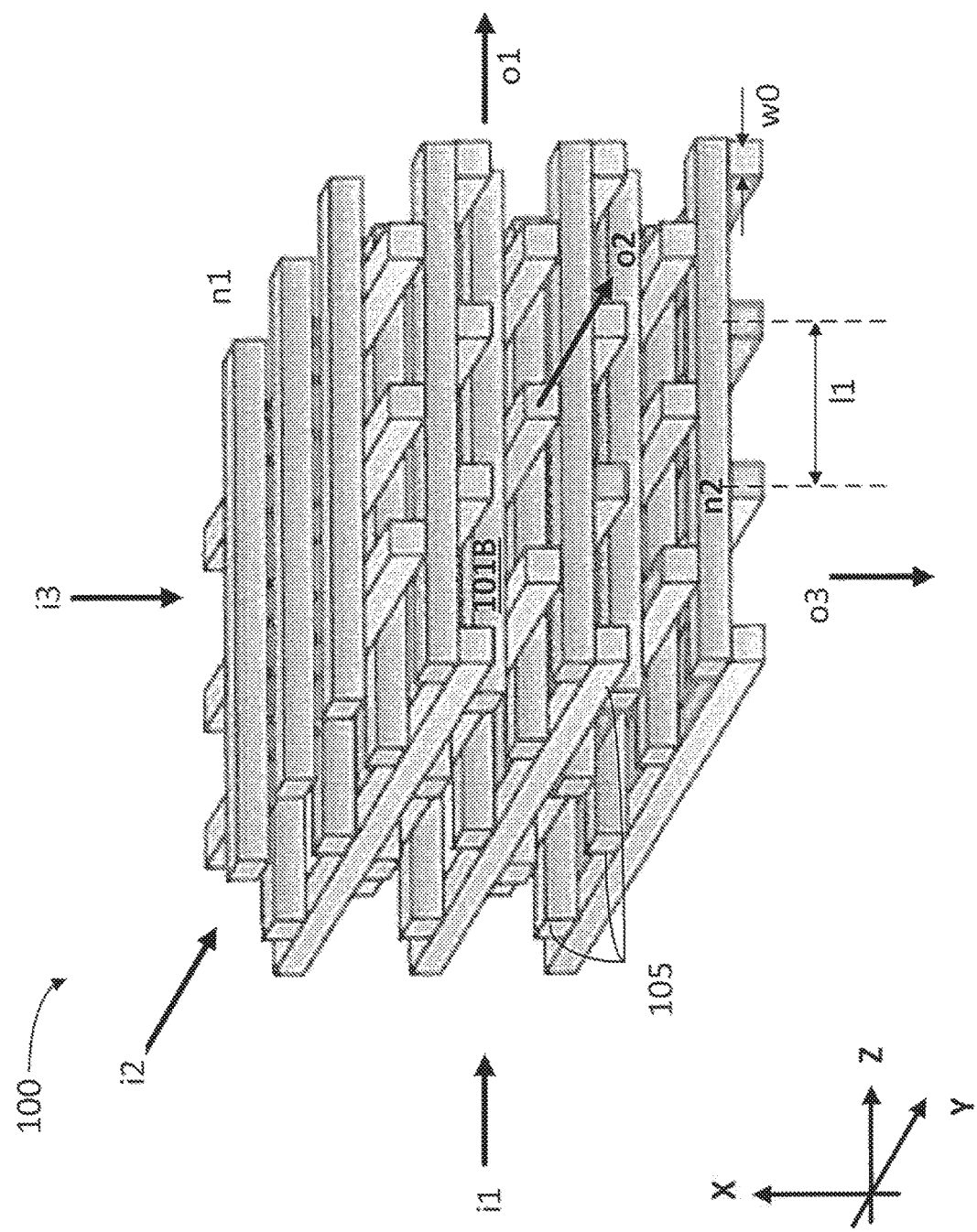
FIG. 1B illustrates a photonic crystal structure including a 3D substrate for use as an ICE.

A PhC-based ICE consistent with embodiments depicted in FIGS. 1A-1D includes a PhC structure having at least one optical input side configured to receive an optical input (e.g., i1, i2, i3), as shown in FIG. 1B, and at least one optical output side configured to receive an optical output (e.g., o1, o2, o3), as also shown in FIG. 1B. Optical input i1 is the input of an incident electromagnetic radiation, and optical output o1 is the output of the transmitted electromagnetic radiation corresponding to i1. Optical inputs i2 and i3 and optical outputs o2 and o3 are likewise related to one another.

Figure 1C:
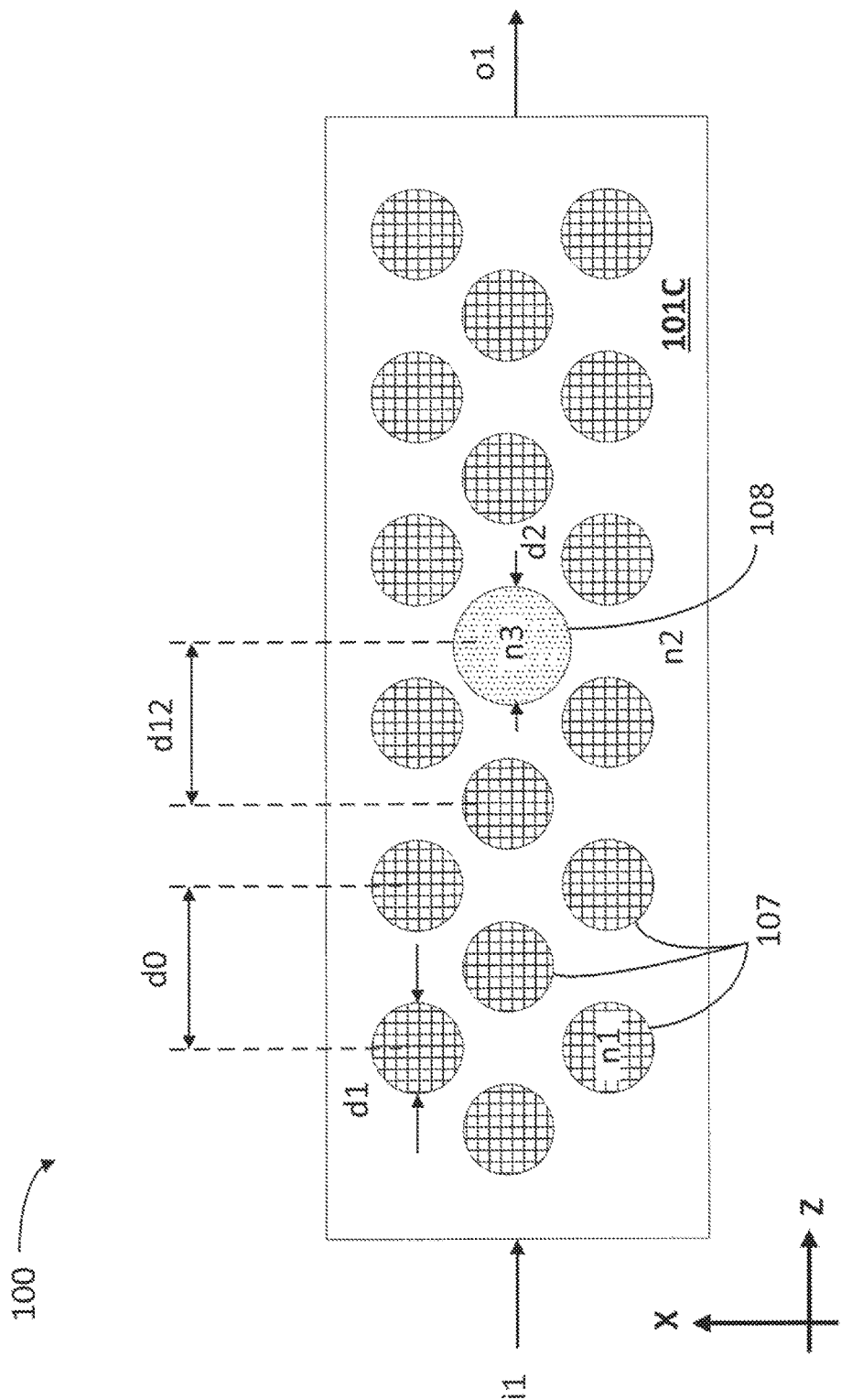
FIG. 1C illustrates a photonic crystal structure including a 2D substrate for use as an ICE.
Figure 1D:
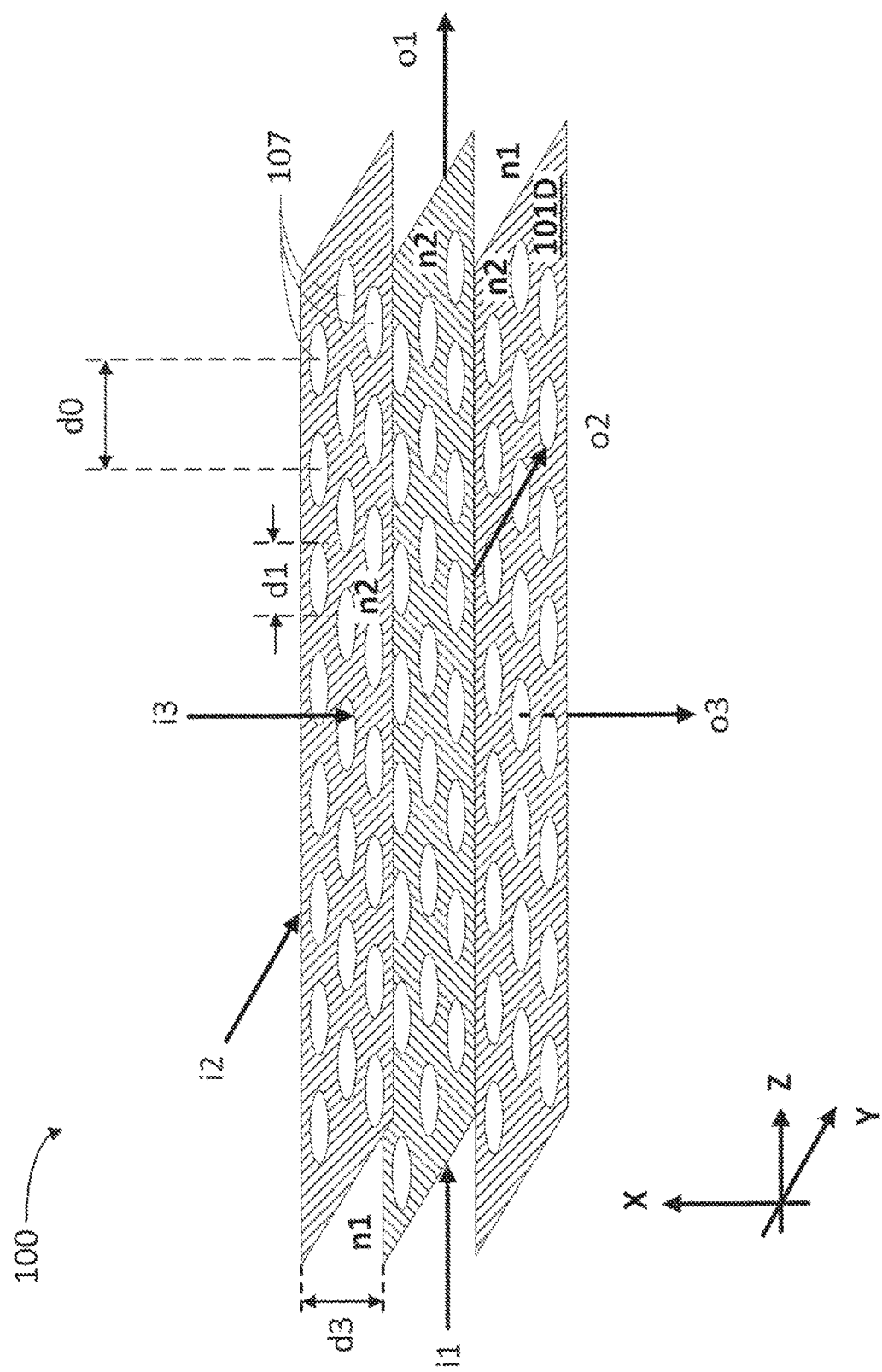
FIG. 1D illustrates an optical configuration for a photonic crystal structure including a 3D substrate for use as an ICE.

As depicted in FIGS. 1B-1D, the PhC structure may include a medium having a first index of refraction (n1), and a substrate embedded in the medium, the substrate having a second index of refraction (n2) and at least one geometric feature. The at least one geometric feature is selected based on an output spectrum resulting from the optical output side. For example, in some embodiments, the output spectrum is such that the optical output has an amplitude proportional to a scalar product of the interacted light and a regression vector for a characteristic of a sample being analyzed. In that regard, the scalar product may include a spectral pattern amplitude and direction of propagation of the interacted light along the PhC structure (cf. FIG. 1A). The scalar product may include a vector formed with the spectral composition of the interacted light and the regression vector. More generally, the output spectrum is a transmission spectrum from an electromagnetic radiation transmitted from the optical input side to the optical output side, and may be dependent of the direction of propagation of the electromagnetic radiation across the PhC structure. In some embodiments, for a pre-determined direction of propagation of the interacted radiation in the PhC structure, the output spectrum is such that the optical output has an amplitude proportional to a scalar product of the interacted light (propagating along the pre-determined direction and a regression vector for the characteristic of the sample being analyzed.

FIG. 1A illustrates an optical configuration 150 for a PhC structure including a 3D substrate 101A for use in an ICE. In FIG. 1A, a Cartesian coordinate system including three mutually orthogonal axes X, Y, and Z is included for illustration purposes only. No limitations to the scope of the present disclosure should be construed from the specific choice of reference axes X, Y, and Z. Throughout the disclosure, the same orientation will be assumed for the reference frame, unless otherwise stated. Optical configuration 150 includes optical input 106 and any one of optical outputs 110a, 110b, 110c, and 110d (hereinafter collectively referred to as optical outputs 110). Accordingly, the optical input side in 3D substrate 101A may be opposite to the optical output side (optical output 110a), or orthogonal to the optical output side (optical outputs 110b and 110c). In some embodiments, the optical input side and the optical output side of the PhC may be the same (i.e., for optical output 110d). While optical output 110d is illustrated at an angle relative to optical input 106, it is understood that optical output 110d may be parallel to optical input 106 (but in the opposite direction). Accordingly, optical output 110d may form any acute angle relative to the direction of optical input 106.

A PhC-based ICE, as used in embodiments disclosed herein, may include one, two, or more than two optical outputs 110a, 110b, 110c, and 110d. In that regard, PhC substrate 101A may be configured to provide optical outputs 110a, 110b, 110c, and 110d, each having different spectral properties.

FIG. 1B illustrates PhC structure 100 including a 3D substrate 101B for use in a PhC-based ICE, as disclosed herein. Substrate 101B includes a plurality of slabs of dielectric material arranged in a three-dimensional (3D) structure having a symmetry along two substantially orthogonal axes (e.g., Y and Z). The dielectric slabs in substrate 101B have a slab diameter 'w0', and are interspaced in parallel by a distance 'l1'. According to some embodiments, a second array of parallel dielectric slabs is stacked on top of a first array of parallel dielectric slabs, the second array of dielectric slabs being substantially perpendicular to the first array of dielectric slabs. Accordingly, this configuration may be stacked along the X-axis up to a desired thickness.

FIG. 1C illustrates PhC structure 100 including a 2D substrate 101C for use in a PhC-based ICE, as disclosed herein. Substrate 101C may define and otherwise include a plurality of apertures 107 and 108. Accordingly, the geometric features in substrate 101C include a center-to-center distance between at least two apertures 107 (d0), a diameter (d1) of one aperture 107 selected from the plurality of apertures, and a second diameter (d2) of aperture 108. Also, the geometric features in substrate 101C may include a center-to-center distance (d12) between a neighboring aperture 107 and aperture 108. In some embodiments, a thickness (t, along the Z-axis and not shown in FIG. 1C) of 2D substrate 101C may be a geometric feature to be selected according to embodiments disclosed herein.

While the precise shape of apertures 107 and 108 is not limiting, substrate 101C includes circular apertures, which may be simple to form in a practical application. In addition, aperture 108 may include a third index of refraction (n3) for the material forming an interior portion of aperture 108, according to some embodiments.

FIG. 1D illustrates PhC structure 100 including a 3D substrate 101D for use in a PhC-based ICE, as disclosed herein. Substrate 101D includes a plurality of layers of material stacked adjacent to each other, and each of the plurality of layers of material includes a plurality of apertures 107 formed in the substrate. The plurality of apertures 107 for each layer has substantially the same geometrical feature (e.g., center-to-center distance d0 and diameter d1) displaced along the plane of the layer between adjacent layers (e.g., the Y-Z plane). In substrate 101D, the at least one geometric feature includes a distance (d3) between adjacent layers.

Figure 2:
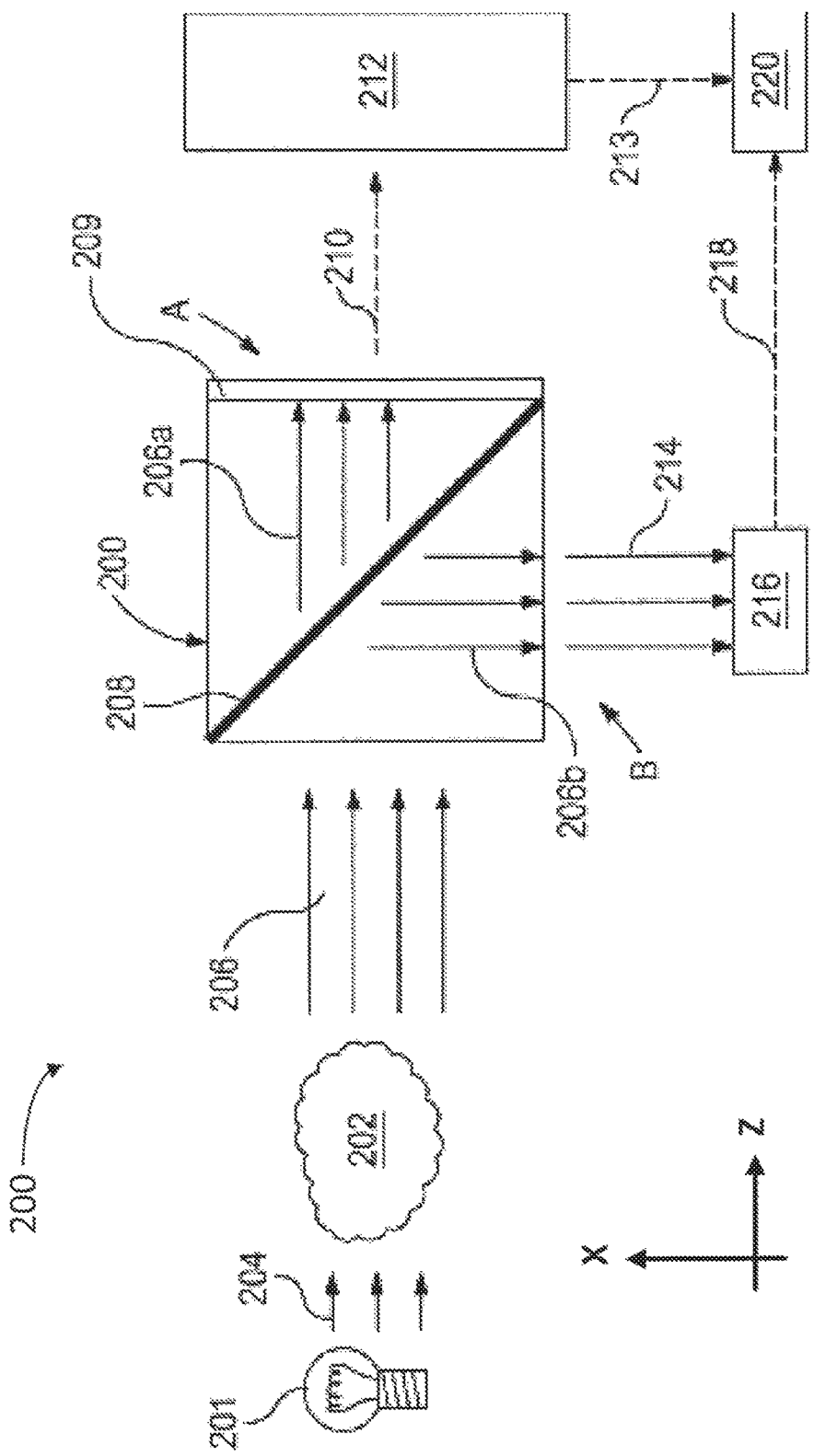
FIG. 2 illustrates an optical computing device including an ICE having a photonic crystal structure.

FIG. 2 illustrates an optical computing device 200 including a PhC-based ICE 209. Optical computing device 200 is able to distinguish electromagnetic radiation related to a characteristic of a sample 202 from other electromagnetic radiation. As shown in FIG. 2, an electromagnetic radiation source 201 emits or otherwise generates electromagnetic radiation 204. Electromagnetic radiation source 201 may be any device capable of emitting or generating electromagnetic radiation, as defined herein. In some embodiments, electromagnetic radiation source 201 is a light bulb, a light emitting device (LED), a laser, a blackbody, a photonic crystal laser, an X-Ray source, or the like. Electromagnetic radiation 204 is directed toward sample 202, which contains an analyte or characteristic of interest desired to be determined. Electromagnetic radiation 204 optically interacts with the sample 202 and produces optically interacted radiation 206 (e.g., sample-interacted light), some of which may be electromagnetic radiation corresponding to the characteristic or analyte of interest and some of which may be background electromagnetic radiation corresponding to other components or characteristics of the sample 202.

While FIG. 2 shows electromagnetic radiation 204 as passing through sample 202 to produce optically interacted radiation 206, it is also contemplated herein to reflect the electromagnetic radiation 204 off the sample 202, such as may be required when sample 202 is translucent, opaque, or solid. Reflecting electromagnetic radiation 204 off the sample 202 also generates optically interacted radiation 206. In some embodiments, electromagnetic radiation source 201 may be omitted altogether from optical computing device 200 and incident electromagnetic radiation may be derived from sample 202 itself. For example, various substances naturally radiate electromagnetic radiation. For instance, sample 202 may be a blackbody radiating substance configured to radiate electromagnetic radiation in the form of heat. In other embodiments, sample 202 may be radioactive or chemo-luminescent and therefore radiate electromagnetic radiation. In some embodiments sample 202 may be a plasma radiating light, such as a flare or a flame resulting from hydrocarbon combustion. In yet other embodiments, the required electromagnetic radiation may be induced from the sample 202 by being acted upon mechanically, magnetically, electrically, combinations thereof, or the like.

Optically interacted radiation 206 impinges upon optical computing device 200, which may contain, for example, a beam splitter 208. The beam splitter 208 may be configured to split the optically interacted radiation 206 into a first beam of light 206a directed in a first channel A and a second beam of light 206b directed in a second channel B. As used herein, the term "channel" refers generally to an optical path or optical train, as known in the art. The first channel A is configured to direct the first beam of light 206a toward the PhC-based ICE 209, thus the first channel A may be characterized as or otherwise called a "primary" channel. PhC-based ICE 209 includes a PhC structure 100 having a substrate 101, as described above with reference to FIGS. 1A-IC (e.g., substrate 101a, 101b, and 101c). PhC-based ICE 209 may be configured to produce modified electromagnetic radiation 210 corresponding to the characteristic or analyte of interest. In particular, PhC-based ICE may be configured so that modified electromagnetic radiation 210 has an amplitude and direction that is proportional to a scalar product (e.g., a dot product) between the spectrum of interacted radiation 206 and a regression vector corresponding to the characteristic of interest in the sample 202 being analyzed.

Within the primary channel A, the modified electromagnetic radiation 210 is subsequently conveyed to a detector 212 for quantification. Detector 212 may be any device capable of detecting electromagnetic radiation, and may be generally characterized as an optical transducer. For example, detector 212 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, and/or combinations thereof, or the like, or other detectors known to those skilled in the art.

In some embodiments, detector 212 is configured to produce an output signal 213 in the form of a voltage (or current) that corresponds to the particular characteristic of the sample 202. In at least one embodiment, output signal 213 and an amplitude of the characteristic of sample 202 may be directly proportional. More generally, the relationship between output signal 213 and the amplitude of the characteristic of the sample 202 may correspond to a polynomial function, an exponential function, and/or a logarithmic function, or a combination thereof.

A second beam of light 206b may be directed within the second channel B toward a second detector 216. Second detector 216 may be similar to first detector 212, such as by being any device capable of detecting electromagnetic radiation. Without limitation, second detector 216 may be used to detect radiating deviations stemming from electromagnetic radiation source 201 or other factors affecting sample 202 or the optical path in electromagnetic radiation 204 not related to the characteristic of interest. Undesirable radiating deviations can occur in the intensity of the light in primary channel A due to a wide variety of reasons and causing various negative effects. These negative effects can be particularly detrimental for measurements taken over a period of time. Radiating deviations can include such things as, but not limited to, light intensity fluctuations of the electromagnetic radiation 204. It can also include interference fluctuations, which may scatter or absorb light from the sample 202 as it moves through the interaction space as might occur if a foreign substance such as dirt or dust is entrained within sample 202 or otherwise passes in front of electromagnetic radiation source 201. Radiating deviations can also include a film of material build-up on the windows of the interrogation space that reduce the amount of light reaching detector 216. Without proper compensation, such radiating deviations could result in false readings from primary channel A, and the output signal 213 would no longer be primarily related to the characteristic of interest.

Accordingly, embodiments consistent with the present disclosure compensate for radiating deviations in optically interacted radiation 206 that are not related to the characteristic of interest in sample 202. To achieve this, second detector 216 is configured to generate a compensating signal 218. Compensating signal 218 is generally indicative of radiating deviations of the electromagnetic radiation source 201, and may be used to normalize the output signal 213. Accordingly, the second channel B is typically characterized as or otherwise referred to in the art as a "reference" channel. In some applications, compensating signal 218 and output signal 213 may be transmitted to or otherwise received by a signal processor 220 communicably coupled to detectors 212 and 216. Signal processor 220 may be a computer including a non-transitory machine-readable medium and may be configured to computationally combine compensating signal 218 with output signal 213 to normalize output signal 213 in view of any radiating deviations detected by second detector 216. In some embodiments, computationally combining the output and compensating signals 213, 218 may entail computing a ratio of the two signals 213, 218, thereby essentially computing a ratio of the primary and reference channels A and B (e.g., A/B).

In some embodiments, reference channel B includes detecting a portion of interacted radiation 206 before it strikes PhC-based ICE 209. Some embodiments include spectrally neutral elements (e.g., elements whose transmittance, absorbance, and/or reflectance do not vary substantially with wavelength) in the optical path of reference channel B. Spectrally neutral elements that may be used for reference channel B include neutral density filters and beam splitters, partially transparent masks, front surface Fresnel reflections, combinations thereof, or similar components.

In some embodiments, the concentration of each analyte or the magnitude of each characteristic determined using the optical computing device 200 can be fed into an algorithm run by the signal processor 220. The algorithm may be configured to make predictions on how the characteristics of the sample 202 change if the concentrations of the analytes are changed relative to one another. In some embodiments, the algorithm produces an output that is readable by an operator who can consider the results and make proper adjustments or take appropriate action, if needed, based upon the output.

Figure 3:
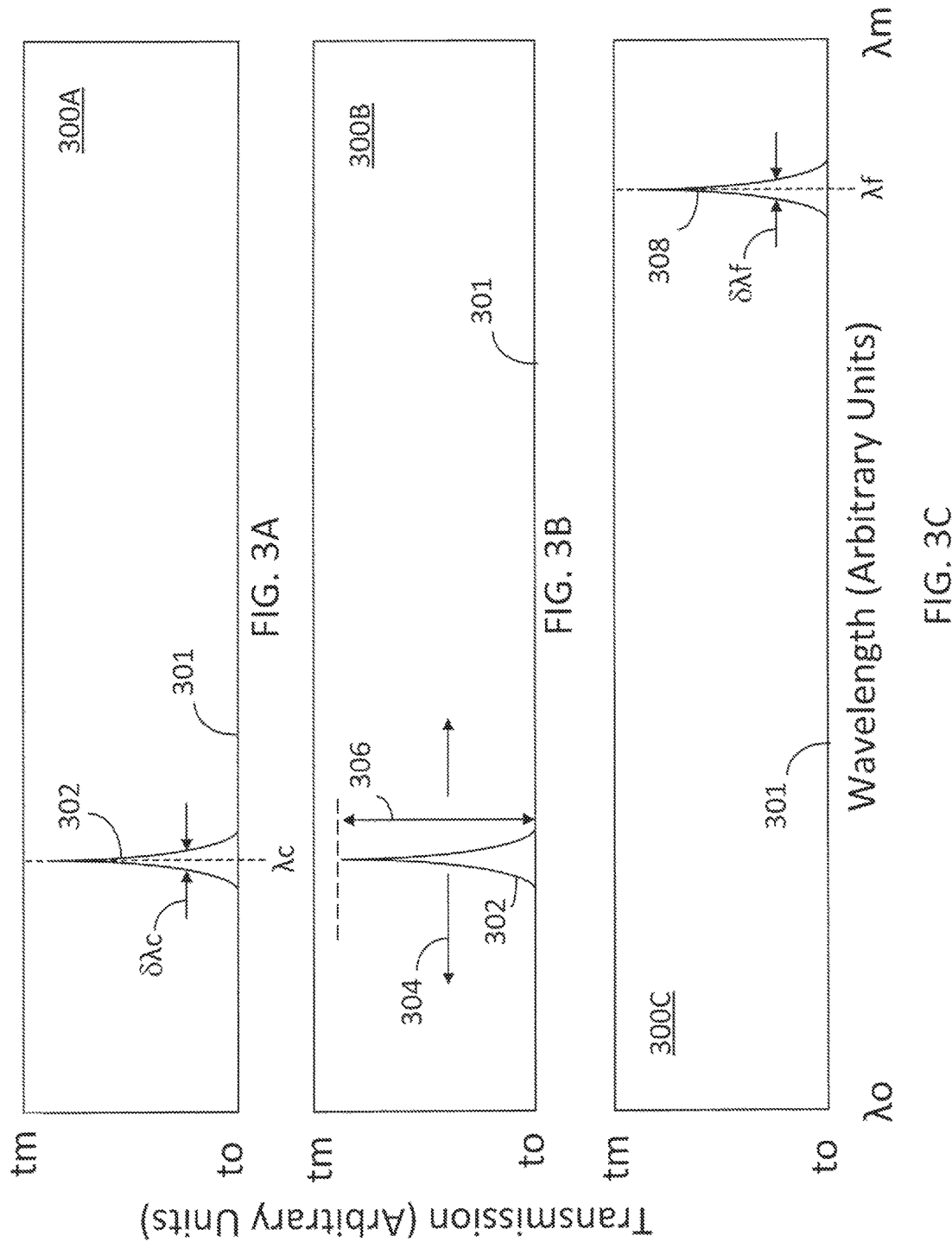
FIG. 3A illustrates a transmission spectrum in a method for fabricating a photonic crystal-based ICE.
FIG. 3B illustrates a transmission spectrum in a method for fabricating a photonic crystal-based ICE.
FIG. 3C illustrates a transmission spectrum in a method for fabricating a photonic crystal-based ICE.

FIG. 3A illustrates a transmission spectrum 300A in a method for fabricating a PhC-based ICE. Transmission spectrum 300A includes an abscissa representing wavelength spanning a range from $\lambda_o$ to $\lambda_m$. The ordinate in transmission spectrum 300A represents a transmission value from a minimum value 'to' (e.g., 0%) to a maximum value 'tm' (e.g., 100%). The dynamic range of a PhC structure having transmission spectrum 300A is determined by to and tm. In embodiments consistent with the present disclosure it is desirable that the dynamic range be as high as possible, meaning that a ratio tm/to be desirably higher.

Transmission spectrum 300A may be a starting point for addressing an analyte of interest in the sample. Transmission spectrum 300A includes a spectral feature 302 (e.g., a band-pass feature) having a center wavelength $\lambda c$, and a bandwidth, $\delta\lambda c$. Accordingly, transmission spectrum 300A also includes a 'stop band' 301. Stop band 301 includes wavelengths where light transmission is close to the minimum value to. In some embodiments, transmission spectrum 300A may result from a 2D PhC including a row of eight circular apertures, similar to substrate 101B in FIG. 1B.

FIG. 3B illustrates a transmission spectrum 300B in another method for fabricating a PhC-based ICE. In spectrum 300B, a transmission dynamic range 306 and a center wavelength 304 in spectral feature 302 may be arbitrarily adjusted to improve a predictive power of a PhC-based ICE in a database of calibrated samples. The SEC, sensitivity and SNR corresponding to transmission spectrum 300B are then calculated using the database of calibrated samples. In that regard, the database of calibrated samples may include a transmission spectrum for each of the calibrated samples associated with a 'true' value for the amplitude of the characteristic of the corresponding sample.

FIG. 3C illustrates a transmission spectrum 300C in another method for fabricating a PhC-based ICE. When the predictive power estimated with spectrum 300B increases (as defined by the merit function), a new transmission spectrum 300C is selected. In some embodiments, transmission spectrum 300C is selected such that a minor adjustment in bandwidth, $\delta\lambda f$ transmission dynamic range, or center wavelength $\lambda f$ may reduce the predictive power. A computer algorithm using a Finite Difference Time Domain (FDTD) method is used to solve Maxwell's equations for individual 'cells' in a partition of the PhC structure. The FDTD method matches the boundary conditions for the electromagnetic field across the cells. The output of the FDTD includes a transmission function of the light propagating through the PhC. Transmission spectrum 300C is fed into an electromagnetic equation propagation FDTD algorithm. The FDTD algorithm takes the transmission spectrum 300C as a target and iteratively modifies the geometrical characteristics of the PhC to find a structure that produces a transmission spectrum comparable to 300C within a selected tolerance value.

Some embodiments use a difference equation method to modify and simulate a PhC structure instead of, or in addition to, an FDTD method. Other methods that may be used in accordance with embodiments disclosed herein include a transfer matrix method, a plane wave expansion method, a Bloch wave method, and the like.

Accordingly, some of the parameters that the FDTD algorithm may modify include, without limitation, the number of apertures in a substrate, the diameter of the apertures in the substrate, the spacing between the apertures in the substrate, and the like (e.g., w0, l1, d1, d2, and d3, in substrates 101B-C of FIGS. 1B-1C, respectively). Further, the FDTD algorithm may adjust the index of refraction of the substrate and the index of refraction of the medium (e.g., n0, n1, and n2 in FIGS. 1B-1D). The resulting PhC structure may include a first sequence of holes at a first diameter, with a gap in the sequence, and a second sequence of holes at a second diameter (e.g., smaller) with a second gap. In some embodiments, a single spectral feature 308 as shown in FIG. 3C may provide a sufficiently predictive PhC-based ICE that is simple to fabricate. However, in some embodiments it may be desirable to introduce new spectral features in the transmission spectrum to obtain an enhanced predictive power of the PhC-based ICE.

Figure 4:
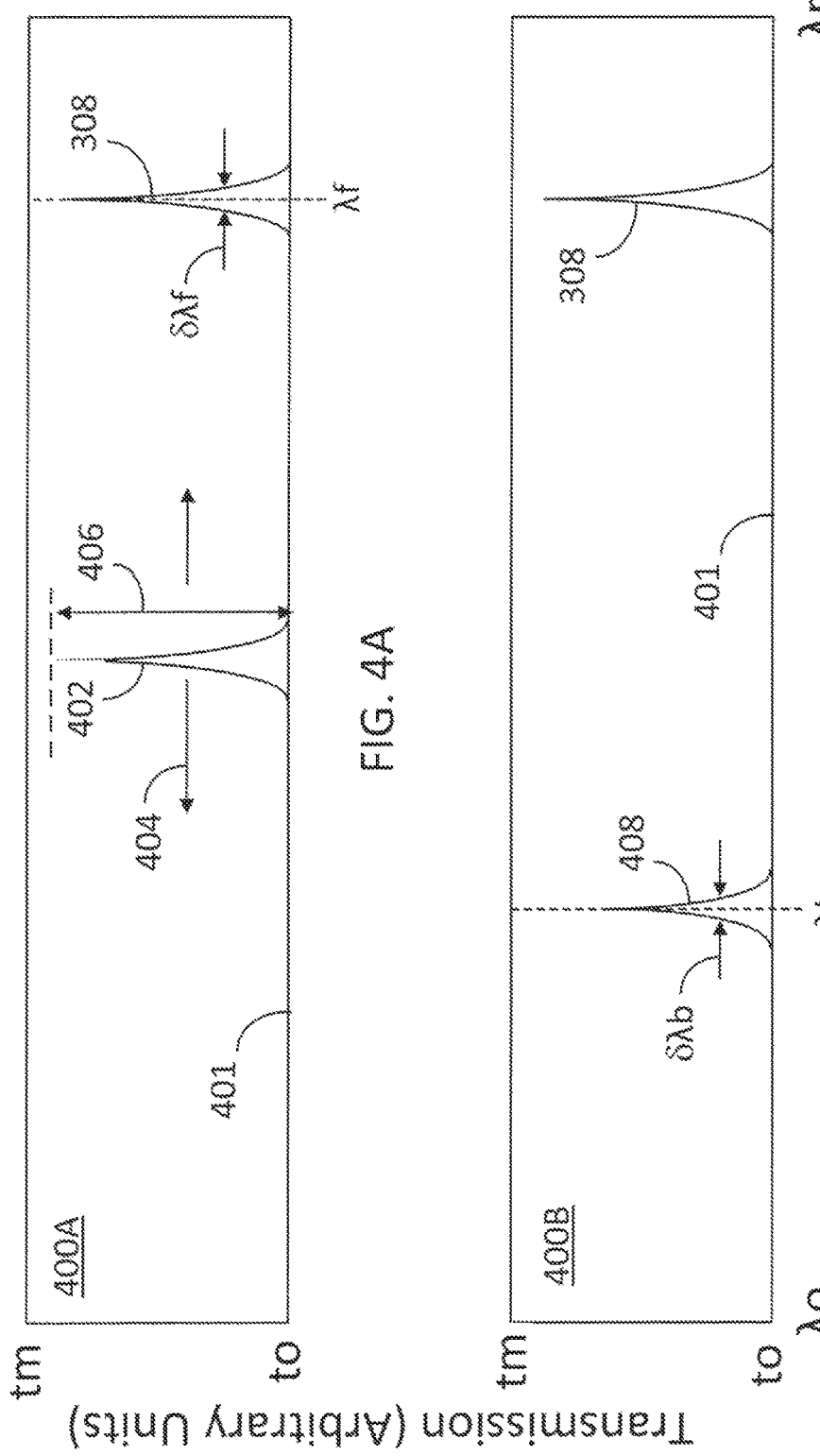
FIG. 4A illustrates a transmission spectrum including two transmission peaks in a method for fabricating a photonic crystal-based ICE.
FIG. 4B illustrates a transmission spectrum including two transmission peaks in a method for fabricating a photonic crystal-based ICE.

FIG. 4A illustrates a transmission spectrum 400A including transmission peaks 308 and 402 in a method for fabricating a PhC-based ICE. Transmission peak 402 may be introduced in transmission spectrum 400A to further improve the predictive power of a PhC-based ICE, according to some embodiments. When a center wavelength ($\lambda f$) and a bandwidth ($\delta \lambda f$) of transmission peak 308 has been determined, in some embodiments second transmission peak 402 further enhances the predictive power of the PhC-based ICE. Accordingly, methods consistent with the present disclosure include steps for adjusting a transmission dynamic range 406 relative to stop band 401. In addition, methods consistent with the present disclosure include displacing a center wavelength 404 of second transmission peak 402 to obtain a transmission spectrum 400B with an enhanced predictive power. Further, according to some embodiments, methods consistent with the present disclosure include steps to adjust the bandwidth of transmission peak 402.

FIG. 4B illustrates transmission spectrum 400B including transmission peaks 308 and 408 in a method for fabricating a PhC-based ICE. In some embodiments, introducing second spectral feature 402 in the model dramatically increases the predictive power of the resulting PhC-based ICE. Accordingly, second spectral feature 402 may result with a center wavelength $\lambda b$ and a bandwidth $\delta \lambda b$ for a transmission spectrum 400B providing an enhanced predictive power to the PhC-based ICE. For example, a sensitivity value may be substantially increased in comparison with a transmission spectrum including a single spectral feature 308.

Figure 5:
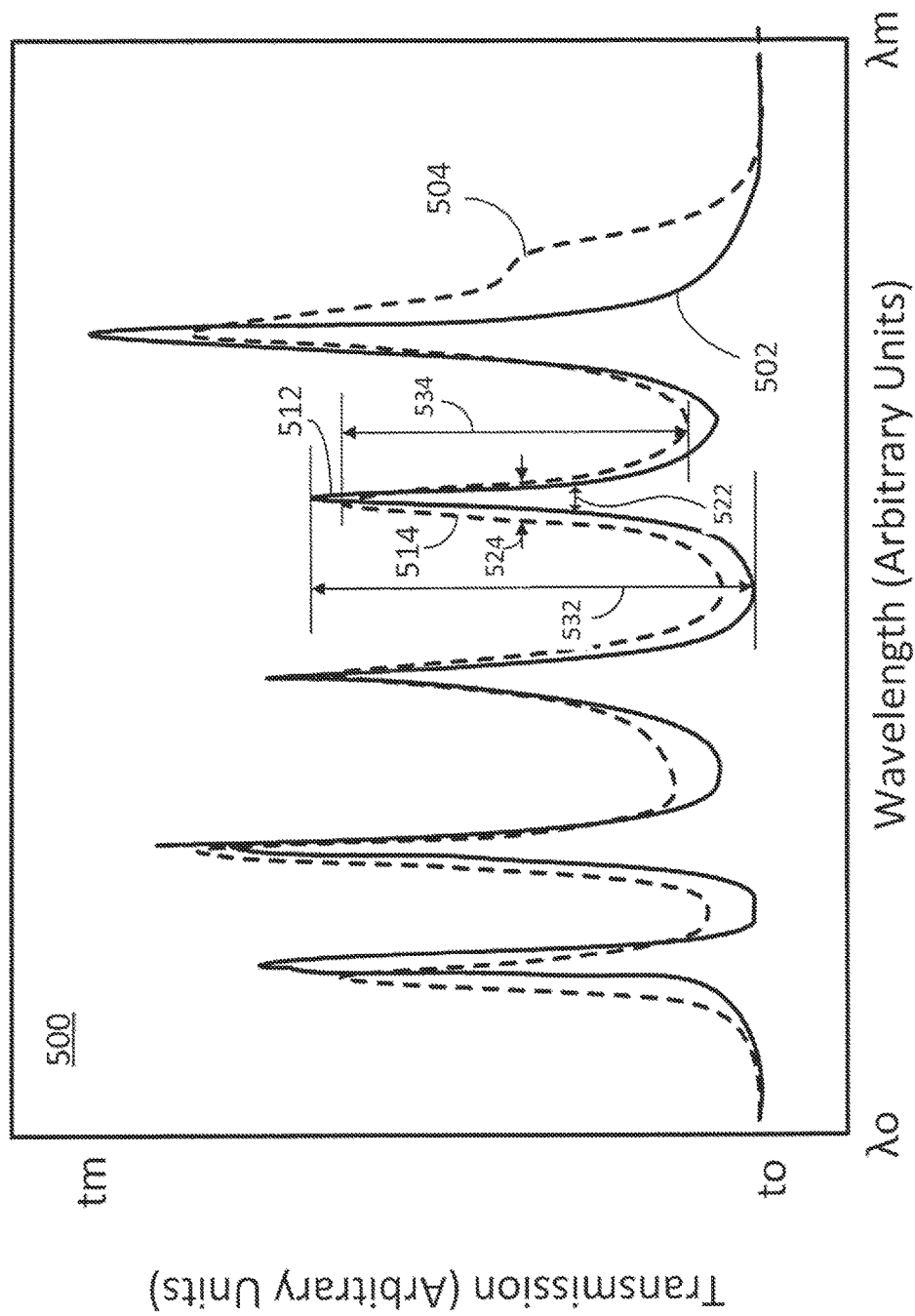
FIG. 5 illustrates a chart including a transmission spectrum from a photonic crystal-based ICE and a multi-layered interference element.

FIG. 5 illustrates a chart 500 including a transmission spectrum 502 from a PhC-based ICE and a transmission spectrum 504 from a multi-layered interference element. Transmission spectra 502 and 504 are selected according to the spectral properties of a particular physical or chemical characteristic of a substance being analyzed. In some embodiments, transmission spectra 502 and 504 are selected such that a detector signal is proportional to a scalar product (e.g., a dot product) between a spectral vector of an interacted light and a linear regression vector associated with the characteristic of the sample being analyzed (e.g., interacted light 206, signal 213 and detector 212, cf. FIG. 2). In that regard, transmission spectra 502 and 504 may be obtained from a multivariate regression analysis including a plurality of calibrated samples in a database. Accordingly, transmission spectra 502 and 504 may be an approximation to a theoretically calculated spectrum obtained using multivariate regression algorithms.

While transmission spectrum 504 may correspond to an ICE having a good predictive power, transmission spectrum 502 may correspond to a PhC-based ICE having an even better predictive power. For example, spectral feature 512 in transmission spectrum 502 has a higher transmission dynamic range 532 and a narrower bandwidth 522 than the transmission dynamic range 534 and bandwidth 524 of spectral feature 514 from transmission spectrum 504. As discussed above, these factors typically are associated with a higher predictive power for any given multivariate regression analysis.

Figure 6:
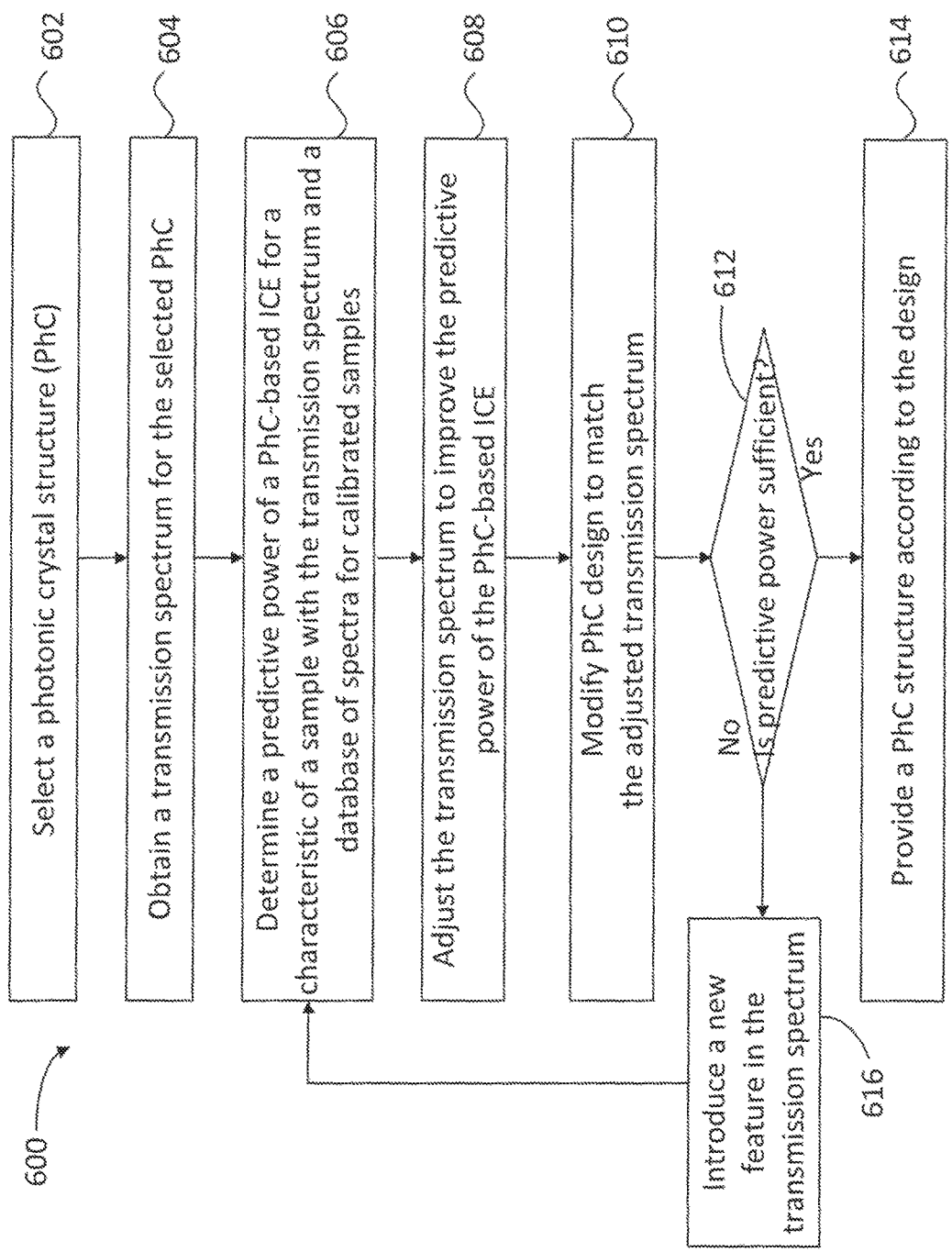
FIG. 6 illustrates a flow chart including steps in a method for fabricating an optical computing device including a photonic crystal-based ICE.

FIG. 6 illustrates a flow chart including steps in a method 600 for fabricating an optical computing device including a PhC-based ICE as disclosed herein. The PhC-based ICE in method 600 may include a PhC structure having an optical input side configured to receive interacted light and an optical output side configured to receive an optical output (e.g., PhC structures 101A-D, cf. FIGS. 1A-D). The PhC may further include a medium having a first index of refraction; and a substrate embedded in the medium, the substrate having a second index of refraction and at least one geometric feature (e.g., refraction indices n1, n2, n3, geometric features w0, l1, d0, d1, d2, d12, and d3, cf. FIGS. 1B-1D, and thickness, t). Furthermore, in some embodiments the at least one geometric feature is selected based on an output spectrum resulting from the optical output side (e.g., transmission spectra 300C. 400B, and 502, cf. FIGS. 3C, 4B and 5). Accordingly, the transmission spectrum may include a band-pass feature (e.g., band pass features 302, 402 and 512 cf. FIG. 3C and FIGS. 4B and 5). In some embodiments, the optical output has an amplitude proportional to a scalar product of the interacted light and a regression vector for a characteristic of a sample being analyzed.

Steps in method 600 may be performed at least partially by a computer including a processor circuit executing commands stored in a memory circuit. When the processor circuit executes the commands, it causes the computer to perform partially or completely at least some of the steps in method 600. Moreover, embodiments consistent with the present disclosure may include at least one, but not all of the steps illustrated in FIG. 6. Further, in some embodiments within the scope of the present disclosure a method may include at least some of the steps in FIG. 6 performed in a different sequence, or even partially or totally overlapping in time.

Step 602 includes selecting a PhC structure. In some embodiments, step 602 includes selecting an optical input side and an optical output side of the PhC structure and selecting a PhC medium having a first index of refraction. Furthermore, in some embodiments step 602 includes selecting at least one geometric feature in the PhC substrate embedded in the medium wherein the PhC substrate may have a second index of refraction. In some embodiments, step 602 includes comparing an output spectrum resulting at the optical output side of the PhC with a regression vector for a characteristic of a sample being analyzed.

Step 604 includes obtaining a transmission spectrum for the selected PhC. In some embodiments, step 604 includes using an electromagnetic equation propagation FDTD algorithm to determine the transmission spectrum of an incident electromagnetic radiation impinging on an optical input side of the PhC structure.

Step 606 includes determining a predictive power of a PhC-based ICE for a characteristic of the sample with the transmission spectrum and a database of spectra for calibrated samples. In some embodiments, step 606 includes performing a multivariate regression analysis of transmission spectra for calibrated samples stored in the database, using the obtained transmission spectrum of the PhC structure. Step 606 may also include any one of the steps of finding a SEC, finding a sensitivity, and finding an SNR using the multivariate regression analysis. Step 606 may further include sorting through a plurality of PhC structures generated by a design suite based on prediction error and signal. In some embodiments, the plurality of PhC structures may be sorted based on their SEC as tested against known values for the characteristic or analyte of interest. For example, the SEC for each photonic crystal structure may be calculated by taking the square root of the sum of squares between known values for the analyte of interest and predicted values as derived from the transmission spectrum of the particular photonic crystal structure.

Step 608 includes adjusting the transmission spectrum to improve the predictive power of a PhC-based ICE with the database. In some embodiments, step 608 includes reducing a prediction error, or reducing a standard error of calibration.

Further, in some embodiments step 608 includes reducing a standard error of prediction, increasing a sensitivity or increasing a slope of a calibration curve. Moreover, in some embodiments step 608 also includes increasing a SNR and increasing a mean optical transmission value as tested against a known value for the characteristic of interest. More specifically, step 608 may include displacing a center wavelength of the band-pass of an electromagnetic radiation transmitted through the PhC, increasing a transmission dynamic range of the band-pass of the electromagnetic radiation transmitted through the PhC, and adjusting the bandwidth of the band-pass of the electromagnetic radiation transmitted through the PhC.

Step 610 includes determining the PhC that produces the adjusted transmission spectrum. In some embodiments, step 610 includes using a recursive algorithm together with the electromagnetic equation propagation FDTD algorithm in order to 'build back' the PhC structure from a transmission spectrum. Step 610 may include using a design suite configured to process and/or optimize a photonic crystal structure based on several "figures of merit" or performance criteria for the ICE. Such performance criteria may include, but are not limited to, minimum prediction error, SEC, standard error of performance (SEP), sensitivity, slope of the calibration curve, SNR, and mean transmission value corresponding to the particular characteristic or analyte of interest. Accordingly, step 610 may include varying physical parameters in the PhC structure such as center-to-center hole distance, or hole diameter, or any combination of the two, until one or more PhC structures meet one or more minimum criteria for predicting an analyte of interest. In fact, a plurality of photonic crystal structures may be selected in a first stage, according to the above.

Step 612 includes determining whether the predictive power of the modified PhC design is sufficient for the purposes of measuring the physical or chemical characteristic of the substance being analyzed. In some embodiments, step 612 includes determining whether the predicted power has reached a maximum with the number of spectral features used up to that point (e.g., one spectral feature in a first iteration of method 600). A spectral feature in a method consistent with method 600 may include a band-pass feature, as disclosed herein. When the predictive power is sufficient according to step 612, step 614 includes providing the PhC structure according to the design. Accordingly, in some embodiments, step 614 includes forming a 2D or a 3D PhC structure such as structures 101A, 101B, and 101C illustrated in FIGS. 1A-1C.

When the predictive power is not sufficient according to step 612, step 616 includes introducing a new spectral feature in the transmission spectrum (e.g., a new band-pass feature, or a new narrow spectral transmission peak in the wavelength range of interest). In some embodiments, method 600 is repeated again from step 606 until the answer in step 612 is 'yes' and step 614 is accomplished. Once a single peak transmission function (as shown in FIG. 3C) is found, a second peak combined with the first peak as a new transmission function (shown in FIG. 4B) is inputted into the FDTD algorithm. A new photonic crystal structure whose transmission function matches the inputted transmission function (with two peaks) is found. The second peak is then incrementally moved in wavelength space in both directions, as shown in FIG. 4B. The SEC, sensitivity and SNR are then calculated by projecting the new transmission function onto the calibration database. If an improvement in SEC, sensitivity and SNR (as defined by a merit function) is seen, then the new transmission function (with two or more peaks) is fed into the FDTD algorithm and steps 606 through 612 are repeated, where a new PhC structure is found whose transmission function matches the inputted transmission function.

In some embodiments, steps 606 through 616 continue for multiple peaks until a global minimum for a merit function is found. The merit function can be the SEC, sensitivity, SNR etc. or a combination of all. The design resulting in step 614 may include any number of peaks (or resonant modes) and any number of stop bands (or photonic band-gaps). In some embodiments, step 614 includes configuring a PhC-based ICE with the PhC structure for a sensor in one of a measurement-while-drilling tool or a logging-while-drilling tool. In some embodiments, step 614 includes configuring the PhC-based ICE with the PhC structure for a sensor in a wireline tool.

In some embodiments, a 'forward design process' may include at least one or more of the steps as described in detail in reference to method 600. A forward design process defines a plurality of PhC structures (2D and higher order) providing reasonable merit function values. More generally, transmission functions in accordance with embodiments disclosed herein could be broadband (e.g., transmission spectrum 502, cf. FIG. 5). Here, the forward design process may include changing the PhC geometry such as the number of apertures, the diameter of apertures, and the center-to-center spacing of the apertures, to determine the transmission function. The performance of the PhC-based ICE is measured using the resulting transmission function. The method then determines whether there is a performance improvement (e.g., a more powerful predictive PhC-based ICE).

In some embodiments, a 'reverse design process' may be used in which an optimal, or close to optimal, transmission function is determined first. Then, the reverse design process finds the PhC structure that produces the optimal, or close to optimal, transmission function. Embodiments of a reverse design process may include method 700, described in detail below in relation to FIG. 7.

Figure 7:
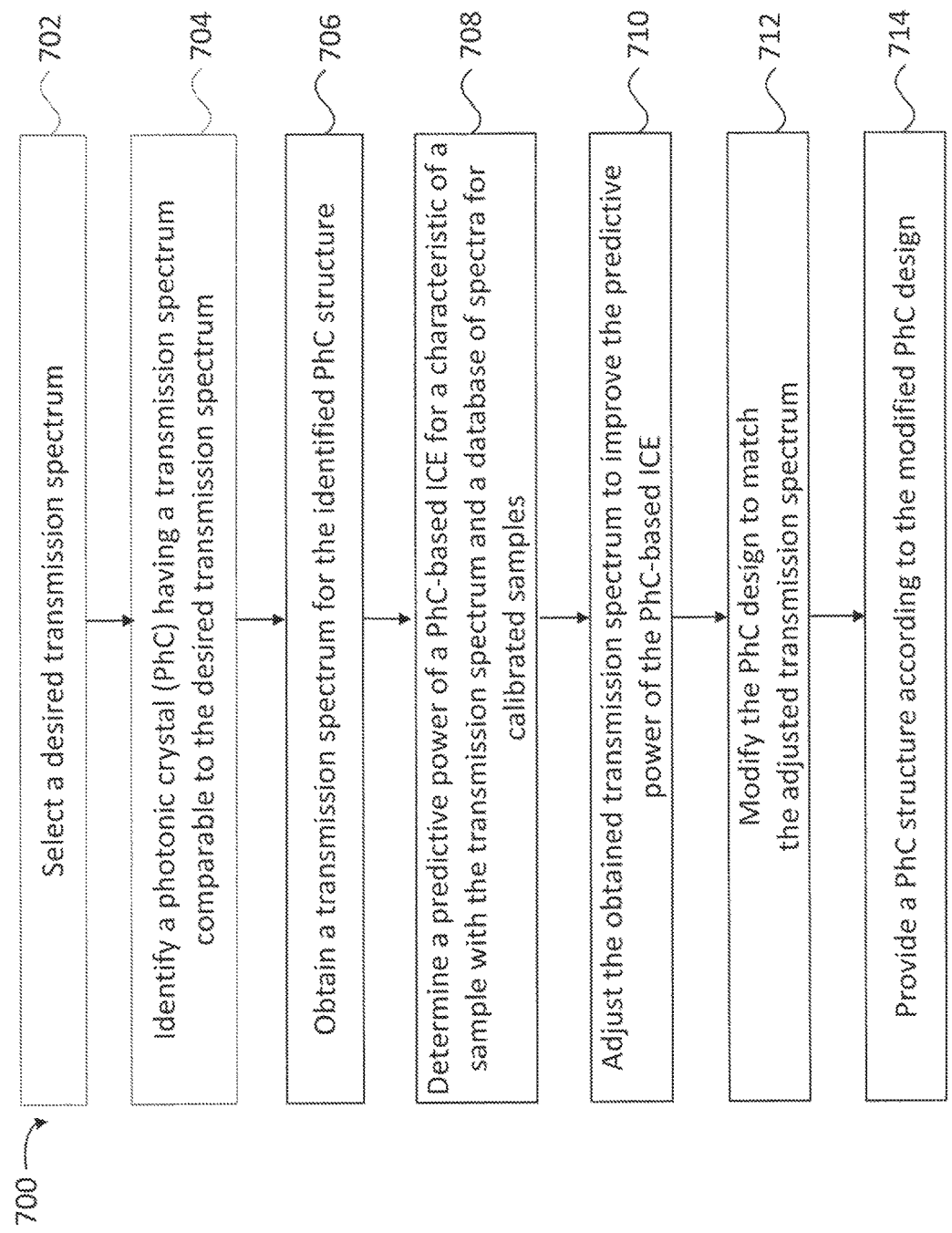
FIG. 7 illustrates a flow chart including steps in a method for fabricating an optical computing device including a photonic crystal-based ICE.

FIG. 7 illustrates a flow chart including steps in a method 700 for fabricating an optical computing device including a PhC-based ICE. The PhC-based ICE in method 700 may include a PhC structure having an optical input side configured to receive interacted light and an optical output side configured to receive an optical output (e.g., PhC structures 101A-D, cf. FIGS. 1A-D). The PhC may further include a medium having a first index of refraction; and a substrate embedded in the medium, the substrate having a second index of refraction and at least one geometric feature (e.g., refraction indices n1, n2, n3, geometric features w0, l1, d0, d1, d2, d12, and d3, cf. FIGS. 1B-1D, and thickness, t). Furthermore, in some embodiments the at least one geometric feature is selected based on an output spectrum resulting from the optical output side (e.g., transmission spectra 300C, 400B, and 502, cf. FIGS. 3C, 4B and 5). Accordingly, the transmission spectrum may include a band-pass feature or narrow band transmission peaks (e.g., band-pass features 302 and 402, cf. FIGS. 3A-3C and FIGS. 4A-4B). In some embodiments, the optical output has an amplitude proportional to a scalar product of the interacted light and a regression vector for a characteristic of a sample being analyzed.

Steps in method 700 may be performed at least partially by a computer including a processor circuit executing commands stored in a memory circuit. When the processor circuit executes the commands, it causes the computer to perform partially or completely at least some of the steps in method 600. Moreover, embodiments consistent with the present disclosure may include at least one, but not all of the steps illustrated in FIG. 7. Further, in some embodiments within the scope of the present disclosure a method may include at least some of the steps in FIG. 7 performed in a different sequence, or even partially or totally overlapping in time.

Step 702 includes selecting a desired transmission spectrum. Accordingly, in some embodiments step 702 may include solving a multivariate regression analysis for a plurality of transmission spectra stored in a database of calibrated samples. The result of step 702 may include a highly refined transmission spectrum (e.g., transmission spectrum 502, cf. FIG. 5). For example, the transmission spectrum may include pass-band features having a high transmission dynamic range, a narrow bandwidth, and a precisely defined center wavelength.

Step 704 includes identifying a PhC having a transmission spectrum comparable to the desired transmission spectrum. In some embodiments, step 610 includes using a recursive algorithm together with the electromagnetic equation propagation FDTD algorithm in order to 'build back' the PhC structure from the desired transmission spectrum.

Step 706 includes obtaining a transmission spectrum for the identified PhC. In some embodiments, step 706 includes using an electromagnetic equation propagation FDTD algorithm to determine the transmission spectrum of an incident electromagnetic radiation impinging on an optical input side of the PhC structure.

Step 708 includes determining a predictive power of a PhC-based ICE for a characteristic of the sample with the transmission spectrum and a database of spectra for calibrated samples. Accordingly, step 708 may include solving a multivariate regression problem using transmission spectra of a plurality of calibrated samples in the database. Furthermore, step 708 may include determining performance criteria for the obtained transmission spectrum. Such performance criteria may include, but are not limited to, minimum prediction error, SEC, SEP, sensitivity, slope of the calibration curve. SNR, and mean transmission value corresponding to the particular characteristic or analyte of interest.

Step 710 includes adjusting the obtained transmission spectrum to improve a predictive power of a PhC-based ICE according to the database. Accordingly, step 710 may include displacing a center wavelength of the band-pass of an incident electromagnetic radiation, increasing a transmission dynamic range of the band-pass of the electromagnetic radiation, and adjusting the bandwidth of the band-pass of the electromagnetic radiation.

Step 712 includes modifying the PhC design to match the adjusted transmission spectrum. Accordingly, step 712 may include varying physical parameters in the PhC structure such as center-to-center hole distance, or hole diameter, or any combination of the two, until one or more PhC structures meet one or more performance criteria for predicting an analyte of interest. In fact, a plurality of PhC structures may be selected in a first stage, according to the above.

Step 714 includes providing a PhC structure according to the modified PhC design. In some embodiments, step 714 includes configuring a PhC-based ICE with the PhC structure for a sensor in one of a measurement-while-drilling tool or a logging while drilling tool. In some embodiments, step 714 includes configuring the PhC-based ICE with the PhC structure for a sensor in a wireline tool.

Figure 8:
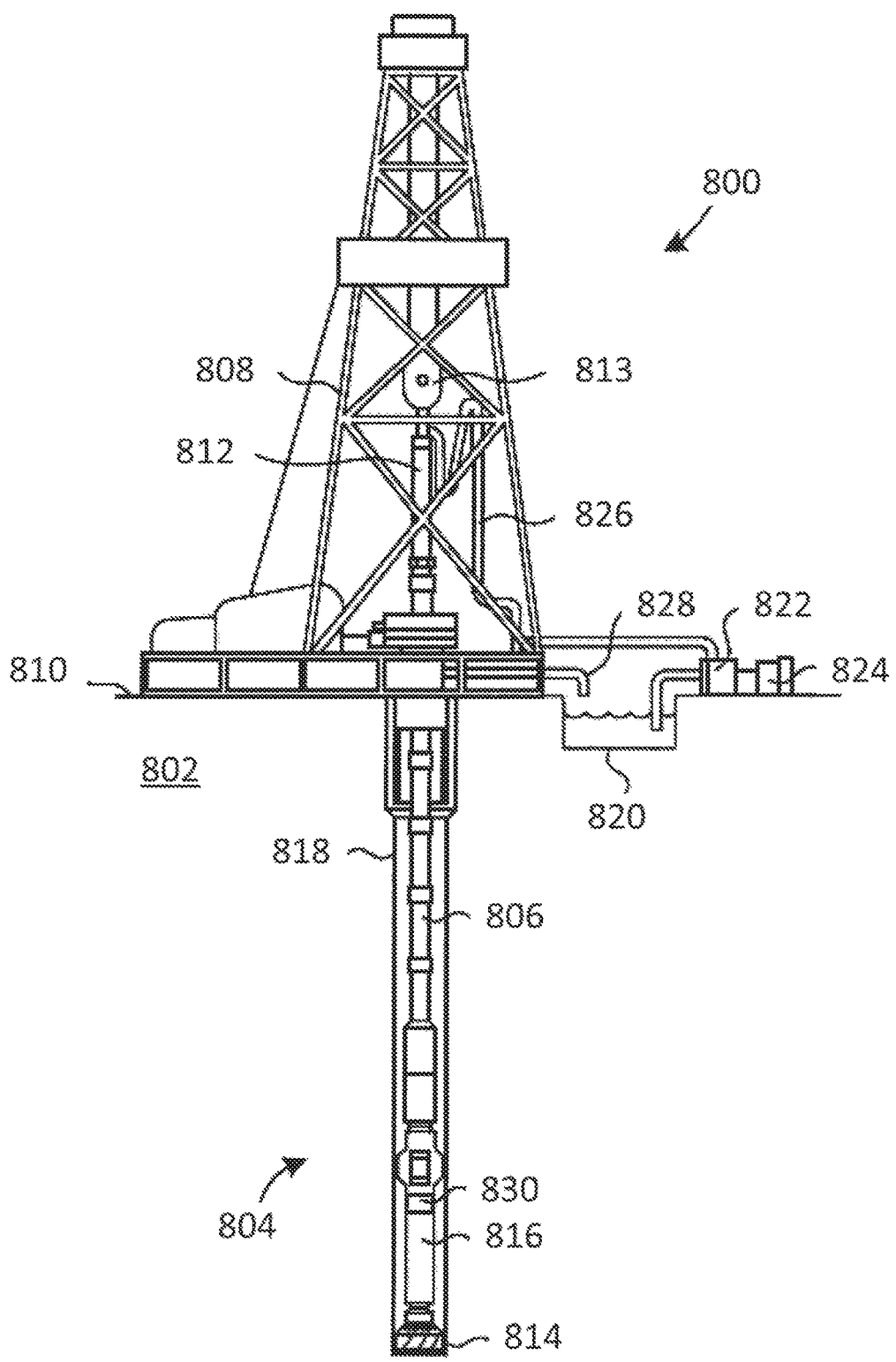
FIG. 8 is a drilling system configured to use an optical sensor for modifying a drilling parameter or configuration in a measurement-while-drilling (MWD) and a logging-while-drilling (LWD) operation.

FIG. 8 is a drilling system 800 configured to use an optical sensor for modifying a drilling parameter or configuration in a measurement-while-drilling (MWD) and a logging-while-drilling (LWD) operation. Boreholes may be created by drilling into the earth 802 using the drilling system 800. The drilling system 800 may be configured to drive a bottom hole assembly (BHA) 804 positioned or otherwise arranged at the bottom of a drill string 806 extended into the earth 802 from a derrick 808 arranged at the surface 810. The derrick 808 includes a Kelly 812 and a traveling block 813 used to lower and raise the Kelly 812 and the drill string 806.

The BHA 804 may include a drill bit 814 operatively coupled to a tool string 816 which may be moved axially within a drilled wellbore 818 as attached to the drill string 806. During operation, the drill bit 814 penetrates the earth 802 and thereby creates the wellbore 818. The BHA 804 provides directional control of the drill bit 814 as it advances into the earth 802. The tool string 816 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within the tool string 816, as shown in FIG. 8.

Fluid or "mud" from a mud tank 820 may be pumped downhole using a mud pump 822 powered by an adjacent power source, such as a prime mover or motor 824. The mud may be pumped from the mud tank 820, through a stand pipe 826, which feeds the mud into the drill string 806 and conveys the same to the drill bit 814. The mud exits one or more nozzles arranged in the drill bit 814 and in the process cools the drill bit 814. After exiting the drill bit 814, the mud circulates back to the surface 810 via the annulus defined between the wellbore 818 and the drill string 806, and in the process returns drill cuttings and debris to the surface. The cuttings and mud mixture are passed through a flow line 828 and are processed such that a cleaned mud is returned down hole through the stand pipe 826 once again.

The BHA 804 may further include a downhole tool 830 that may be similar to the downhole tools described herein. More particularly, downhole tool 830 may have a sensor with an optical computing system as disclosed herein (e.g., optical computing system 200, cf. FIG. 2). Accordingly, the optical computing system in tool 830 may include a PhC-based ICE optimized to obtain an improved predictive power.

Figure 9:
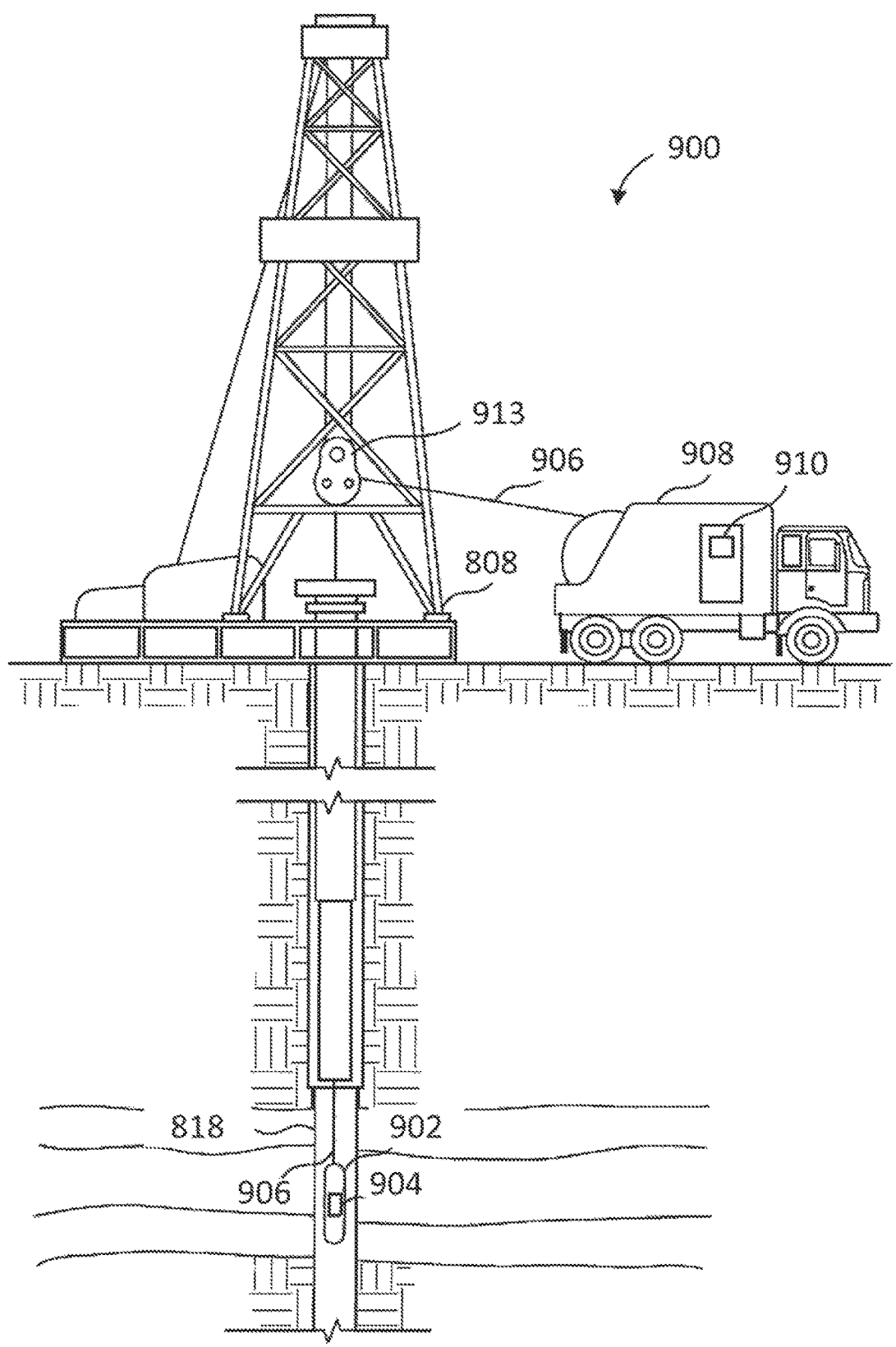
FIG. 9 is a wireline system configured to use an optical sensor during formation testing and sampling.

FIG. 9 is a wireline system 900 configured to use an optical sensor during formation testing and sampling. In some embodiments, wireline system 900 may be configured to use a calibrated optical sensor during formation testing and sampling. After drilling of wellbore 818 is complete, it may be desirable to know more details of types of formation fluids and the associated characteristics through sampling with use of wireline formation tester. System 900 may include a downhole tool 902 that forms part of a wireline logging operation that can include one or more optical sensors 904, as described herein, as part of a downhole measurement tool. System 900 may include the derrick 808 that supports the traveling block 813. Wireline logging tool 902, such as a probe or sonde, may be lowered by wireline or logging cable 906 into the borehole 818. Tool 902 may be lowered to the bottom of the region of interest and subsequently pulled upward at a substantially constant speed. Tool 902 may be configured to measure fluid properties of the wellbore fluids, and any measurement data generated by downhole tool 902 and its associated optical sensors 904 can be communicated to a surface logging facility 908 for storage, processing, and/or analysis. Any one of optical sensors 904 may include an optical computing system having a PhC-based ICE for enhanced predictive power, according to embodiments disclosed herein (e.g., optical computing system 200, cf. FIG. 2). Logging facility 908 may be provided with electronic equipment 910, including processors for various types of signal processing.

Those skilled in the art will readily appreciate that the methods described herein, or large portions thereof, may be automated at some point such that a computerized system may be programmed to design, predict, and fabricate PhC-based ICEs with higher predictive power. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A method that includes selecting a photonic crystal (PhC) structure with a design suite stored in a non-transitory, computer-readable medium, obtaining a transmission spectrum for the PhC structure, determining a predictive power of a PhC-based integrated computational element (ICE) for a characteristic of a sample with the transmission spectrum and a database of spectra for calibrated samples, adjusting the transmission spectrum to improve the predictive power, and fabricating the PhC structure for the PhC-based ICE when the predictive power surpasses a pre-selected threshold.

B. A method that includes selecting a desired transmission spectrum for an integrated computational element (ICE), identifying a photonic crystal (PhC) structure having a transmission spectrum comparable to the desired transmission spectrum, obtaining the transmission spectrum for the PhC structure, determining a predictive power of a PhC-based ICE for a characteristic of a sample with the obtained transmission spectrum and a database of spectra for calibrated samples, adjusting the transmission spectrum of the PhC structure to improve the predictive power of the PhC-based ICE, and fabricating the PhC structure for the PhC-based ICE when the predictive power surpasses a pre-selected threshold.

C. An integrated computational element (ICE) that includes a photonic crystal (PhC) structure having an optical input side configured to receive interacted light and an optical output side configured to receive an optical output, the PhC comprising a medium having a first index of refraction, and a substrate embedded in the medium, the substrate having a second index of refraction and at least one geometric feature, wherein the at least one geometric feature is selected based on an output spectrum resulting from the optical output side, and wherein the optical output has an amplitude proportional to a scalar product of the interacted light and a regression vector for a characteristic of a sample being analyzed.

Each of embodiments A, B, and C may have one or more of the following additional elements in any combination: Element 1: wherein fabricating the PhC structure further comprises finding a PhC structure having a transmission function similar to the adjusted transmission function. Element 2: wherein adjusting the transmission spectrum to improve the predictive power comprises one of reducing a prediction error, reducing a standard error of calibration, reducing a standard error of prediction, increasing a sensitivity, increasing a slope of a calibration curve, increasing a signal-to-noise ratio, and increasing a mean optical transmission value as tested against a known value for the characteristic of the sample. Element 3: wherein adjusting the transmission spectrum to improve the predictive power comprises one of displacing a center wavelength of a band-pass of an electromagnetic radiation transmitted through the PhC structure, increasing a transmission dynamic range of the band-pass of the electromagnetic radiation transmitted through the PhC structure, and adjusting the bandwidth of the band-pass of the electromagnetic radiation transmitted through the PhC structure. Element 4: wherein selecting a PhC structure further comprises selecting an optical input side and an optical output side of the PhC structure, selecting a PhC medium having a first index of refraction, and selecting at least one geometric feature in a PhC substrate embedded in the medium, the PhC substrate having a second index of refraction, wherein selecting at least one geometric feature comprises comparing an output spectrum resulting at the optical output side of the PhC with a regression vector for a characteristic of a sample being analyzed. Element 5: wherein the second index of refraction is different from the first index of refraction. Element 6: further comprising configuring the PhC-based ICE for a sensor in one of a measurement-while-drilling tool or a logging-while-drilling tool. Element 7: further comprising configuring the PhC-based ICE for a sensor in a wireline tool.

Element 8: wherein fabricating the PhC structure further comprises finding a PhC structure having a transmission function similar to the adjusted transmission function. Element 9: wherein adjusting the transmission spectrum of the PhC structure comprises at least one of modifying a geometric feature of the PhC structure, modifying an index of refraction of a medium in the PhC structure, and modifying an index of refraction of a substrate in the PhC structure. Element 10: wherein the PhC structure comprises a 2D substrate, the method further comprising selecting a center-to-center distance in a plurality of apertures on the 2D substrate based on the corresponding power of prediction. Element 11: further comprising estimating a detector signal from an interacted light transmitted through the PhC structure, wherein selecting a desired transmission spectrum comprises determining that the detector signal is proportional to a scalar product between the interacted light and a linear regression vector associated with the characteristic of the sample being analyzed. Element 12: wherein fabricating the PhC structure for the PhC-based ICE comprises selecting at least one geometric feature in a PhC substrate embedded in a medium based on a comparison of an output spectrum resulting at an optical output side of the PhC with a regression vector for a characteristic of a sample being analyzed. Element 13: wherein selecting the at least one geometric feature comprises selecting a diameter for an aperture in a plurality of apertures formed on the PhC substrate. Element 14: further comprising configuring the PhC-based ICE for a sensor in one of a measurement-while-drilling tool or a logging-while-drilling tool. Element 15: further comprising configuring the PhC-based ICE for a sensor in a wireline tool.

Element 16: wherein the output spectrum is a transmission spectrum from an electromagnetic radiation transmitted from the optical input side to the optical output side. Element 17: wherein the at least one geometric feature comprises one of a center-to-center distance between at least two apertures from a plurality of apertures formed in the substrate, a first diameter of a first aperture selected from the plurality of apertures, and a second diameter of a second aperture selected from the plurality of apertures. Element 18: wherein the substrate comprises a plurality of slabs of dielectric material arranged in a three-dimensional (3D) structure having a symmetry along two substantially orthogonal axes, and wherein the at least one geometric feature is a slab diameter. Element 19: wherein the substrate comprises a plurality of layers of material stacked adjacent to each other, and each of the plurality of layers of material comprises a plurality of apertures formed in the substrate, wherein the plurality of apertures formed in the substrate for each layer has substantially the same one geometric feature displaced along the plane of the layer between adjacent layers. Element 20: wherein the apertures are circular, and further wherein the at least one geometric feature comprises a distance between adjacent layers.

By way of non-limiting example, exemplary combinations applicable to A, B, and C include: Element 4 with Element 5; Element 12 with Element 13: and Element 19 with Element 20.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method, comprising:
    selecting a photonic crystal (PhC) structure with a design suite stored in a non-transitory, computer-readable medium;
    obtaining a transmission spectrum for the PhC structure;
    determining a predictive power of a PhC-based integrated computational element (ICE) for a characteristic of a sample with the transmission spectrum and a database of spectra for calibrated samples;
    adjusting the transmission spectrum to improve the predictive power; and
    fabricating the PhC structure for the PhC-based ICE when the predictive power surpasses a pre-selected threshold.

2. The method of claim 1, wherein said selected PhC structure has a transmission function of light propagating through the PhC structure, said adjusting the transmission spectrum including adjusting the transmission function of the selected PhC structure, and wherein fabricating the PhC structure further comprises finding a PhC structure having a transmission function similar to the adjusted transmission function.

3. The method of claim 1, wherein adjusting the transmission spectrum to improve the predictive power comprises one of reducing a prediction error, reducing a standard error of calibration, reducing a standard error of prediction, increasing a sensitivity, increasing a slope of a calibration curve, increasing a signal-to-noise ratio, and increasing a mean optical transmission value as tested against a known value for the characteristic of the sample.

4. The method of claim 1, wherein adjusting the transmission spectrum to improve the predictive power comprises one of displacing a center wavelength of a band-pass of an electromagnetic radiation transmitted through the PhC structure, increasing a transmission dynamic range of the band-pass of the electromagnetic radiation transmitted through the PhC structure, and adjusting the bandwidth of the band-pass of the electromagnetic radiation transmitted through the PhC structure.

5. The method of claim 1, wherein selecting a PhC structure further comprises:
   selecting an optical input side and an optical output side of the PhC structure;
   selecting a PhC medium having a first index of refraction; and
   selecting at least one geometric feature in a PhC substrate embedded in the medium, the PhC substrate having a second index of refraction, wherein selecting at least one geometric feature comprises comparing an output spectrum resulting at the optical output side of the PhC with a regression vector for a characteristic of a sample being analyzed.

6. The method of claim 5, wherein the second index of refraction is different from the first index of refraction.

7. The method of claim 1, further comprising configuring the PhC-based ICE for a sensor in one of a measurement-while-drilling tool or a logging-while-drilling tool.

8. The method of claim 1, further comprising configuring the PhC-based ICE for a sensor in a wireline tool.

9. A method, comprising:
   selecting a desired transmission spectrum for an integrated computational element (ICE);
   identifying a photonic crystal (PhC) structure having a transmission spectrum comparable to the desired transmission spectrum;
   obtaining the transmission spectrum for the PhC structure;
   determining a predictive power of a PhC-based ICE for a characteristic of a sample with the obtained transmission spectrum and a database of spectra for calibrated samples;
   adjusting the transmission spectrum of the PhC structure to improve the predictive power of the PhC-based ICE; and
   fabricating the PhC structure for the PhC-based ICE when the predictive power surpasses a pre-selected threshold.

10. The method of claim 9, wherein said selected PhC structure has a transmission function of light propagating through the PhC structure, said adjusting the transmission spectrum including adjusting the transmission function of the selected PhC structure, and wherein fabricating the PhC structure further comprises finding a PhC structure having a transmission function similar to the adjusted transmission function.

11. The method of claim 9, wherein adjusting the transmission spectrum of the PhC structure comprises at least one of modifying a geometric feature of the PhC structure, modifying an index of refraction of a medium in the PhC structure, and modifying an index of refraction of a substrate in the PhC structure.

12. The method of claim 9, wherein the PhC structure comprises a 2D substrate, the method further comprising selecting a center-to-center distance in a plurality of apertures on the 2D substrate based on the corresponding power of prediction.

13. The method of claim 9, further comprising estimating a detector signal from an interacted light transmitted through the PhC structure, wherein selecting a desired transmission spectrum comprises determining that the detector signal is proportional to a scalar product between the interacted light and a linear regression vector associated with the characteristic of the sample being analyzed.

14. The method of claim 9, wherein fabricating the PhC structure for the PhC-based ICE comprises selecting at least one geometric feature in a PhC substrate embedded in a medium based on a comparison of an output spectrum resulting at an optical output side of the PhC with a regression vector for a characteristic of a sample being analyzed.

15. The method of claim 14, wherein selecting the at least one geometric feature comprises selecting a diameter for an aperture in a plurality of apertures formed on the PhC substrate.

16. The method of claim 9, further comprising configuring the PhC-based ICE for a sensor in one of a measurement-while-drilling tool or a logging-while-drilling tool.

17. The method of claim 9, further comprising configuring the PhC-based ICE for a sensor in a wireline tool.

18. A computer system comprising:
   a processor; and
   a memory device that stores commands executed by the processor to perform a method comprising:
      selecting a photonic crystal (PhC) structure with a design suite stored in a non-transitory, computer-readable medium;
      obtaining a transmission spectrum for the PhC structure;
      determining a predictive power of a PhC-based integrated computational element (ICE) for a characteristic of a sample with the transmission spectrum and a database of spectra for calibrated samples;
      adjusting the transmission spectrum to improve the predictive power; and
      providing the PhC structure for the PhC-based ICE when the predictive power surpasses a pre-selected threshold.

19. The computer system of claim 18, wherein adjusting the transmission spectrum to improve the predictive power comprises one of displacing a center wavelength of a band-pass of an electromagnetic radiation transmitted through the PhC structure, increasing a transmission dynamic range of the band-pass of the electromagnetic radiation transmitted through the PhC structure, and adjusting the bandwidth of the band-pass of the electromagnetic radiation transmitted through the PhC structure.

20. The computer system of claim 18, wherein the method further includes:
   selecting an optical input side and an optical output side of the PhC structure;
   selecting a PhC medium having a first index of refraction; and
   selecting at least one geometric feature in a PhC substrate embedded in the medium, the PhC substrate having a second index of refraction, wherein selecting at least one geometric feature comprises comparing an output spectrum resulting at the optical output side of the PhC with a regression vector for a characteristic of a sample being analyzed.

21. A computer system comprising:
   a processor; and
   a memory device that stores commands executed by the processor to perform a method comprising:
      selecting a desired transmission spectrum for an integrated computational element (ICE);
      identifying a photonic crystal (PhC) structure having a transmission spectrum comparable to the desired transmission spectrum;
      obtaining the transmission spectrum for the PhC structure;

determining a predictive power of a PhC-based ICE for a characteristic of a sample with the obtained transmission spectrum and a database of spectra for calibrated samples;

adjusting the transmission spectrum of the PhC structure to improve the predictive power of the PhC-based ICE; and fabricating the PhC structure for the PhC-based ICE when the predictive power surpasses a pre-selected threshold.

22. The computer system of claim 21, wherein the PhC structure comprises a 2D substrate, the method further comprising selecting a center-to-center distance in a plurality of apertures on the 2D substrate based on the corresponding power of prediction.

23. The computer system of claim 21, wherein the method further comprises estimating a detector signal from an interacted light transmitted through the PhC structure, and wherein selecting a desired transmission spectrum comprises determining that the detector signal is proportional to a scalar product between the interacted light and a linear regression vector associated with the characteristic of the sample being analyzed.

* * * * *